United States Patent
Shirakawa et al.

(10) Patent No.: US 9,925,259 B2
(45) Date of Patent: Mar. 27, 2018

(54) IMMUNOGENIC POLYPEPTIDE SURFACE LAYER-EXPRESSING BIFIDOBACTERIUM

(71) Applicant: NATIONAL UNIVERSITY CORPORATION KOBE UNIVERSITY, Hyogo (JP)

(72) Inventors: Toshiro Shirakawa, Hyogo (JP); Hak Hotta, Hyogo (JP); Takane Katayama, Ishikawa (JP)

(73) Assignee: National University Corporation Kobe University, Hyogo (JP)

( * ) Notice: Subject to any disclaimer, the term of this patent is extended or adjusted under 35 U.S.C. 154(b) by 39 days.

(21) Appl. No.: 14/768,508

(22) PCT Filed: Feb. 14, 2014

(86) PCT No.: PCT/JP2014/053560
§ 371 (c)(1),
(2) Date: Aug. 18, 2015

(87) PCT Pub. No.: WO2014/129412
PCT Pub. Date: Aug. 28, 2014

(65) Prior Publication Data
US 2016/0008459 A1    Jan. 14, 2016

(30) Foreign Application Priority Data

Feb. 19, 2013 (JP) ................. 2013-030477

(51) Int. Cl.
| | |
|---|---|
| A61K 39/29 | (2006.01) |
| A61K 39/05 | (2006.01) |
| C07K 14/195 | (2006.01) |
| A61K 35/745 | (2015.01) |
| A61K 39/12 | (2006.01) |
| C12N 7/00 | (2006.01) |
| A61K 39/00 | (2006.01) |

(52) U.S. Cl.
CPC ............ *A61K 39/29* (2013.01); *A61K 35/745* (2013.01); *A61K 39/05* (2013.01); *A61K 39/12* (2013.01); *C07K 14/195* (2013.01); *C12N 7/00* (2013.01); *A61K 39/0011* (2013.01); *A61K 2039/523* (2013.01); *A61K 2039/542* (2013.01); *A61K 2039/585* (2013.01); *C12N 2770/24234* (2013.01)

(58) Field of Classification Search
None
See application file for complete search history.

(56) References Cited

U.S. PATENT DOCUMENTS

| | | | |
|---|---|---|---|
| 6,555,114 B1 | 4/2003 | Leroux-Roels et al. | |
| 7,625,569 B2 | 12/2009 | Duke et al. | |
| 8,758,760 B2 | 6/2014 | Shirakawa et al. | |
| 2007/0054262 A1* | 3/2007 | Baker | C07K 7/06 435/5 |
| 2012/0034256 A1* | 2/2012 | Weiner | A61K 39/29 424/189.1 |
| 2012/0100170 A1 | 4/2012 | Lauer et al. | |
| 2012/0177687 A1* | 7/2012 | Shirakawa | A61K 39/385 424/234.1 |

FOREIGN PATENT DOCUMENTS

| | | |
|---|---|---|
| EP | 979867 | 2/2000 |
| EP | 2479270 | 7/2012 |
| JP | 3642755 | 2/2005 |

OTHER PUBLICATIONS

Yu et al. 2013 (Oral administration of mice using Bifidobacterium longum expressing VP1 protein from enterovirus 71; Arch Viol 158: 1071-1077).*
Yamamoto et al. 2010 (Genetically modified Bifidobacterium displaying *Salmonella antigen* protects mice from lethal challenge of *Salmonella typhimurium* in a murine typhoid fever model; Vaccine 28: 6684-6691).*
Yao et al.; "Molecular views of viral polyprotein processing revealed by the crystal structure of the hepatitis C virus bifunctional protease-helicase"; Structure, 1999, vol. 7, p. 1353-1363.
Cerny et al.; "Cytotoxic T Lymphocyte Response to Hepatitis C Virus-derived Peptides Containing the HLA A2.1 Binding Motif"; J. Clin. Invest., 1995, vol. 95, p. 521-530.
Yamamoto et al.; "Genetically modified Bifidobacterium displaying *Salmonella*-antigen protects mice from lethal challenge of *Salmonella typhimurium* in a murine typhoid fever model"; Vaccine, 2010, vol. 28, p. 6684-6691.
Matsumura et al.; "Construction of *Escherichia coli*—Bifidobacterium longum Shuttle Vector Transforming B. longum 105-A and 108-A"; 34 Biosci. Biotechnol. Biochem., 1997, vol. 61, p. 1211-1212.
Wada et al.; "Purification, crystallization and preliminary X-ray analysis of the galacto-N-biose-/lacto-N-biose I-binding protein (GL-BP) of the ABC transporter from Bifidobacterium longum JCM1217"; Acta Crystallographica Section F., 2007, vol. F63, p. 751.
Sakaguchi et al.; "A targeted gene knockout method using a newly constructed temperature-sensitive plasmid mediated homologous recombination of Bifidobacterium longum"; Appl. Microbiol. Biotechnol., 2012, vol. 95, p. 499-509.

(Continued)

*Primary Examiner* — Mary Lyons
(74) *Attorney, Agent, or Firm* — Renner, Otto, Boisselle & Sklar, LLP

(57) ABSTRACT

Provided is a gene for expressing an immunogenic polypeptide on the cell surface of a *bifidobacterium*, and the gene includes a gene encoding the immunogenic polypeptide, the immunogenic polypeptide includes a predetermined base domain and at least one antigenic peptide, and the at least one antigenic peptide is linked on any of the N-terminal side and the C-terminal side of the base domain. The gene for expressing an immunogenic polypeptide on a cell surface of a *bifidobacterium* of the present invention can further include a gene encoding a *bifidobacterium*-derived GNB/LNB substrate-binding membrane protein.

16 Claims, 9 Drawing Sheets

(56) References Cited

OTHER PUBLICATIONS

Qiu et al.; "Hepatitis C virus-specific cellular and humoral immune responses following immunization with a multi epitope fusion protein"; International Journal of Molecular Medicine, 2012, vol. 29, p. 12-17.

Lang et al.; "Strong HCV NS3- and NS4A-specific cellular immune responses induced in mice and Rhesus macaques by a novel HCV genotype 1a/1b consensus DNA vaccine"; Vaccine, 2008, vol. 26, p. 6225-6231.

H. Yu, et al., "Priming with CpG-enriched plasmid and boosting with protein formulated with CpG oligodeoxynucleotides and Quil A induces strong cellular and humoral Immune responses to hepatitis C Virus NS3", Journal of General Virology, 2004, vol. 85, p. 1533-1543.

S. E. Gogo, et al., "Protective vaccination with hepatitis C Virus NS3 but not core antigen in a novel mouse challenge model", The Journal of Gene Medicine, 2008, vol. 10, p. 177-186.

J. S. zur Wiesch, et al., "Broad Repertoire of the CD4+ Th Cell Response in Spontaneously Controlled Hepatitis C Virus Infection Includes Dominant and Highly Promiscuous Epitopes", The Journal of Immunology, 2005, vol. 175, p. 3603-3613.

T. Mashiba, et al., "Identification of CTL epitopes in hepatitis C Virus by a genome-wide computational scanning and a rational design of peptide vaccine", Immunogenetics, 2007, vol. 59, p. 197-209.

A. M. Wertheimer, et al., "Novel CD4+ and CD8+ T-Cell Determinants Within the NS3 Protein in Subjects With Spontaneously Resolved HCV Infection", Hepatology, 2003, vol. 37, p. 577-589.

K. Ito, et al., "Identification of novel hepatitis C virus-specific cytotoxic T lymphocyte epiotpe in NS3 region", Hepatology Research, 2006, vol. 36, p. 294-300.

F. X. L. Labrador, et al., "The use of class-I HLA tetramers for the detection of hepatitis C Virus NS3-specific CD8+ T cells in patients with chronic infection", Journal of Immunological Methods, 2004, vol. 287, p. 91-99.

C. N. Haefelin, et al., "Analysis of the Evolutionary Forces in an Immunodominant CD8 Epitope in Hepatitis C Virus at a Population Level", Journal of Virology, 2008, vol. 82, No. 7, p. 3438-3451.

A. L. Erickson, et al., "The Outcome of Hepatitis C Virus Infection is Predicted by Escape Mutations in Epitopes Targeted by Cytotoxic T Lymphocytes", Immunity, 2001, vol. 15, p. 883-895.

S. Takei, et al., "Oral administration of genetically modified Bifidobacterium displaying HCV-NS3 multi-epitope fusion protein could induce an HCV-NS3-specific systemic Immune response in mice, Vaccine", 2014, vol. 32, p. 3066-3074.

PCT/JP2014/053560; PCT International Search Report dated May 9, 2014.

PCT/JP2014/053560; International Preliminary Examination Report dated Aug. 20, 2014.

* cited by examiner

Fig.1

/organism="Hepatitis C virus"  HCV-1 b
/clone="MKC1A"    GenBank: BAA08120.1

NS3  a.a. 1027-1657

CD8 epitope

CD4 epitope 1021 qgwrllapit aysqqtrgll gciitsltgr dknqvegevq vvstat<u>gsfl atcingvcwt</u>

1081 <u>vyhgagsktl</u> agpkgpitqm ytnvdqdlvg wpappgarsm tpctcgssd<u>l ylvtrhadvi</u>

1141 <u>pvrrrgdsrg</u> sllsprpisy lkgssggpl<u>l cpsghvvg</u>if raavctrgva kavdfvpves 1201 m<u>ettmrspvf tdnstppavp</u> qsfqvahlha ptgsgkstkv paayaaqgyk vlvlnpsvaa 1261 tlgfgaymsk ahgvdpnirt gvrtittgap <u>itystvqkfl</u> ad<u>ggcsggay diiicdechs</u>

1321 <u>tdstsilgig</u> tvldqaetag arlvvlatat ppgsvtvphp nieevalsnt <u>geipfygkai</u>

1381 pleaikggrh <u>lifchskkkc</u> delaa<u>klsal gvna</u>vayyrg ldvsiiptsg dvvv<u>vatdal</u>

1441 <u>mtgytgdfds vidc</u>ntcvtq tvdfsldptf tietttvpqd avsrsqrrgr tgrgrggiyr 1501 fvtpgerpsg mfdssvlcec ydagcawyel <u>tpaetsvrlr aylntpgl</u>pv cqdhlefwes 1561 vftglthida hflsqtkqag dnfpylvayq atvcarakap ppswdqmwkc lirlkptlhg 1621 ptpllyr<u>lga vgnevtl</u>thp itkfimacms adlevvtstw vlvggvlaal aayclttgsv
 (SEQ. ID. No. 3)

Fig.2

CD8 epitope

CD4 epitope

>1 atgsflatcingvcwtvyhgagsVPVESMETTMRSPVFTDNSTPPAVPQSFQVAHLHAPTGSGKSTK
VPAAYAAQGYKVLVLNPSVAATLGFGAYMSKAHGVDPNIRTGVRTITTGAPITYSTYGKFLADGGCS
GGAYDIIICDECHSTDSTSILGIGTVLDQAETAGARLVVLATATgeipfygkaipldelaaklsalg
vnavatdalmtgytqdfdsvidcnt (SEQ. ID. No. 23)

>2 atgsflatcingvcwtvyhgagsVPVESMETTMRSPVFTDNSTPPAVPQSFQVAHLHAPTGSGKSTK
VPAAYAAQGYKVLVLNPSVAATLGFGAYMSKAHGVDPNIRTGVRTITTGAPITYSTYGKFLADGGCS
GGAYDIIICDECHSTDSTSILGIGTVLDQAETAGARLVVLATATgeipfygkaipl (SEQ. ID. No. 24)

Fig.3

[kDa]
75
                              ←69 kDa
                              ←66 kDa
50
     M    1    2    3

1. Wild type *B. longum*
2. NS3-expressing *B. longum* 2164
3. NS3-expressing *B. longum* 2165

Fig.8

CD8 epitope

CD4 epitope atgsflatcingvcwtvyhgagsGMFDSSVLCECYDAGCAWYELTPAETSVRLRAYLNTPGLPVCQ
DHLEFWESVFTGLTHIDAHFLSQTKQAGDNFPYLVAYQATVCARAKAPPPSWDQMWKCLI
RLKPTLHGPTPLLYRLGAVQNEVTLTHPITKFIMACMSADLEVVTgeipfygkaipldelaaklsalgvn
avatdalmtgytgdfdsvidcnt (SEQ. ID. No. 32)

Fig.9

CD8 epitope

CD4 epitope atgsflatcingvcwtvyhgagsSVTVPHPNIEEVALSNTGEIPFYGKAIPLEAIKGGRHLIFCHSKQLC
DELAAKLSALGVNAVAYYRGLDVSIIPTSGDVVVVATDALMTGYTGDFDSVIDCNTCVTQTV
DFSLDPTFTIETTTVPQDAVSRSQMQGRTGRGRGGIYRFVTPGERPSeltpaetsvrlrayIntpgl
(SEQ. ID. No. 35)

Fig.10

CD8 epitope

CD4 epitope

TGSVVIVGRIILSGITAYSQQTRGLLGCIITSLTGRDKNQVEGEVQVVSTATQSFLATCINGVC
WTVYHGAGSKTLAGPKGPITQMYTNVDQDLVGWPAPPGARSMTPCTCGSSDLYLVTRHA
DVIPVRQLGDSRGSLLSPRPISYLKGSSGGPLLCPSGHVVGIFRAAVCTRGVAKAVDfvpves
mettmrspvftdnstppavpqsfqvahlhaptgsgkstkvpaayaaqgykvivlnpsvaatlgfgaymskahgvdpnirtgvrt
ittgapitystygkfladggcsggaydiiicdechstdstsilgigtvldqaetagarlvvlatatgeipfvgkaipldelaaklsalgvna
vatdalmtgvtgdfdsvldcnt (SEQ. ID. No. 38)

Fig.11

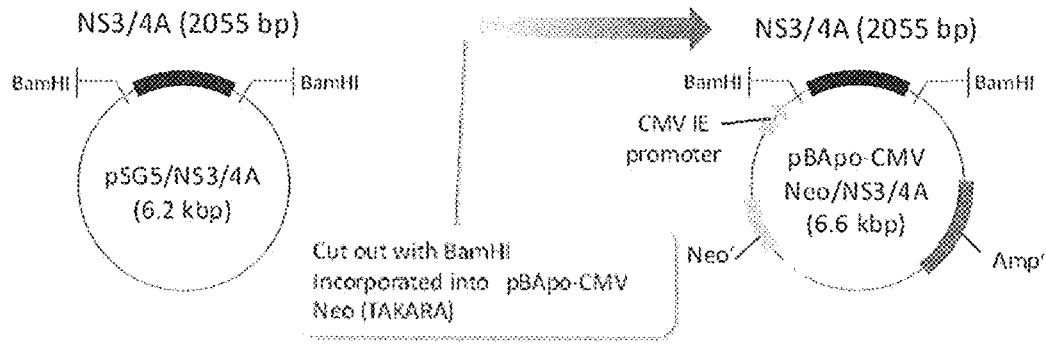

Fig.12

RT-PCR

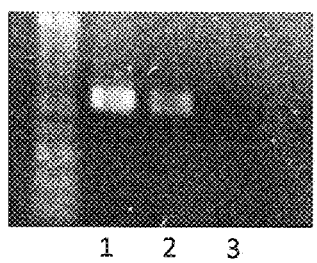

1  2  3

*: vs PBS (p<0.05)   : vs 2012 (p<0.05)   *: vs PBS and 2012 (p<0.05)

IMMUNOGENIC POLYPEPTIDE SURFACE LAYER-EXPRESSING BIFIDOBACTERIUM

The present application is a U.S. National Stage Application under 35 USC § 371 of International Application No. PCT/JP2014/053560, filed 14 Feb. 2014, published as WO 2014/129412 A1 on 28 Aug. 2014, which in turn claims priority to Japanese Application No. 2013-030477, filed 19 Feb. 2013, the entirety of both of which are incorporated herein by reference.

TECHNICAL FIELD

The present invention relates to an immunogenic polypeptide cell surface-expressing bifidobacterium, and more specifically relates to an immunogenic polypeptide cell surface-expressing bifidobacterium with which a hepatitis C vaccine composition can be manufactured, for example.

BACKGROUND ART

There are one hundred and seventy million hepatitis C virus (HCV) carriers or more in the world, approximately 70% of the carriers suffer from chronic hepatitis, who face the risk of hepatic cirrhosis or hepatic cancer. There are approximately two million carriers in Japan as well, and approximately 80% of the carriers have been infected with type 1b.

Interferon therapy is mainly performed as a therapy for hepatitis C. However, a combination therapy where pegylated-interferon α and ribavirin, which is an anti-virus drug, are used in combination has a type 1 virus elimination percentage of 50% or less, a long duration of treatment, and severe side effects, and thus there is a need for the development of a more effective therapeutic drug and the establishment of a therapy.

HCV is a positive-strand RNA virus belonging to the Flaviviridae family, and is constituted by four types of structural protein regions (C-E1-E2-P7) and six types of non-structural protein regions (NS2-NS3-NS4A-NS4B-NS5A-NS5B). Among them, the NS3 protein has serine protease activity on the N-terminal one-third region and RNA helicase activity on the C-terminal two-thirds region. The NS3 protein which has such two activities of protease-helicase has been studied by X-ray crystallography to reveal its conformation (Non-Patent Document 1).

A strong immune response specific to NS3 was observed in patients who recovered from HCV infection (Non-Patent Document 2). Also, the NS3 protein is highly genetically conserved, and many cytotoxic T lymphocyte (CTL) epitopes thereof are identified (Non-Patent Document 3).

Use of a NS3 protein-derived polypeptide for the prevention or treatment of hepatitis C has been reported. For example, Patent Document 1 describes a polypeptide that includes or consists of at least eight-consecutive amino acids derived from amino acids from positions 1188 to 1463 in the NS3 region of HCV, and that includes a T lymphocyte stimulating epitope. Patent Document 2 states that a yeast cell expressing a HCV fusion protein that includes at least a part of a HCV NS3 protease linked to at least a part of the HCV core sequence is used as a base for a vaccine. Patent Document 3 states that a bacterium such as attenuated *Listeria monocytogenes* that expresses and secretes a full-length protein or an immunogenic protein of NS3 or the like is used as a vaccine platform.

On the other hand, the use of transformed microorganisms by genetic engineering as an oral vaccine has attracted attention. It has been reported that a transformed *Bifidobacterium longum* expressing flagellin derived from *Salmonella typhimurium* on the cell surface with a GNB/LNB substrate-binding membrane protein (also referred to as "GLBP" herein), which is present in a cell membrane of microorganisms of the genus *Bifidobacterium* (also referred to as "bifidobacteria" herein), is orally administered to a mouse so that flagellin-specific antibodies are produced in blood to induce systemic immunity via intestinal mucosal immunity, and the lethal effect of mice due to oral infection with *Salmonella typhimurium* is effectively inhibited (Non-Patent Document 4 and Patent Document 4). Also, an oral vaccine, which is an acid-resistant capsule preparation containing transformed *Bifidobacterium longum* that intracellularly expresses, or expresses and secretes flagellin derived from *Salmonella typhimurium*, *Vibrio cholerae*, or *Shigella dysenteriae*, has been reported (Patent Document 5).

PRIOR ART DOCUMENTS

Patent Documents

Patent Document 1: Japanese National Publication No. H9-504534
Patent Document 2: Japanese National Publication No. 2008-516610
Patent Document 3: Japanese National Publication No. 2011-529077
Patent Document 4: WO 2011/034181
Patent Document 5: WO 2008/114889

Non-Patent Document

Non-Patent Document 1: Structure, vol. 7, p. 1353-1363, 1999
Non-Patent Document 2: J. Gene. Med., vol. 10, p. 177-186, 2008
Non-Patent Document 3: J. Clin. Invest., vol. 95, p. 521-530, 1995
Non-Patent Document 4: Vaccine, vol. 28, p. 6684-6691, 2010

SUMMARY OF INVENTION

Problems to be Solved by the Invention

It is an object of the present invention to provide a more effective therapeutic drug for therapy for HCV infection. Furthermore, it is also an object of the present invention to provide an effective therapeutic drug for treating diseases resulting from HCV infection, by means of oral administration. It is also an object of the present invention to provide a method for expressing an immunogenic polypeptide on a cell surface of *bifidobacterium*.

Means for Solving the Problems

The inventors have focused on the immunogenicity of a non-structural protein 3 (NS3), which is a region directed to HCV replication, and has succeeded in the production of bifidobacteria expressing and presenting an HCV antigenic polypeptide on its cell surface by designing a synthetic polypeptide containing a CD4 epitope and a CD8 epitope which are derived from the NS3 protein, and the induction of NS3 specific immune response (that is, induction of NS3 specific intestinal mucosal immunity and systemic humoral immunity, and cell-mediated immunity) in animals orally administered with the HCV antigenic polypeptide cell surface-expressing bifidobacteria. Furthermore, the inventors have found that such a design of synthetic polypeptide can be applied to provide a gene for expressing an immunogenic polypeptide on the cell surface of a *bifidobacterium* which can be widely used for immunogenic polypeptides.

The present invention provides a gene for expressing an immunogenic polypeptide on a cell surface of a *bifidobacterium*, comprising:

a gene encoding the immunogenic polypeptide, wherein the immunogenic polypeptide is a hepatitis C virus antigenic polypeptide comprising a base domain and at least one antigenic peptide, the base domain comprises one or more selected from the group consisting of (1) a polypeptide comprising an amino acid sequence of SEQ. ID. No. 16 or a polypeptide having an amino acid sequence that has at least 90% sequence identity to the amino acid sequence;

(2) a polypeptide comprising an amino acid sequence of SEQ. ID. No. 17 or a polypeptide having an amino acid sequence that has at least 90% sequence identity to the amino acid sequence;

(3) a polypeptide comprising an amino acid sequence of SEQ. ID. No. 18 or a polypeptide having an amino acid sequence that has at least 90% sequence identity to the amino acid sequence; and (4) a polypeptide comprising an amino acid sequence of SEQ. ID. No. 19 or a polypeptide having an amino acid sequence that has at least 90% sequence identity to the amino acid sequence;

the antigenic peptide is at least one selected from the group consisting of peptides comprising amino acid sequences of SEQ. ID. Nos. 4 to 15 and a peptide having an amino acid sequence that has at least 90% sequence identity to an amino acid sequence of SEQ. ID. Nos. 4 to 15, and the at least one antigenic peptide is linked on any of an N-terminal side and a C-terminal side of the base domain.

In one embodiment, (1) the base domain is a polypeptide comprising an amino acid sequence of SEQ. ID. No. 16 or a polypeptide having an amino acid sequence that has at least 90% sequence identity to the amino acid sequence, a region including QSFLATCINGVCWTVYHGAG (SEQ. ID. No. 4) or a peptide having an amino acid sequence that has at least 90% sequence identity to the amino acid sequence being linked on the N-terminal side of the base domain, and a region including EIPFYGKAI (SEQ. ID. No. 7) or a peptide having an amino acid sequence that has at least 90% sequence identity to the amino acid sequence, or a region including EIPFYGKAI (SEQ. ID. No. 7) or a peptide having an amino acid sequence that has at least 90% sequence identity to the amino acid sequence, KLSALGVNA (SEQ. ID. No. 9) or a peptide having an amino acid sequence that has at least 90% sequence identity to the amino acid sequence, and VATDALMTGYTGDFDSVIDC (SEQ. ID. No. 10) or a peptide having an amino acid sequence that has at least 90% sequence identity to the amino acid sequence being linked on the C-terminal side;

(2) the base domain is a polypeptide comprising an amino acid sequence of SEQ. ID. No. 17 or a polypeptide having an amino acid sequence that has at least 90% sequence identity to the amino acid sequence, a region including a peptide comprising QSFLATCINGVCWTVYHGAG (SEQ. ID. No. 4) or a peptide having an amino acid sequence that has at least 90% sequence identity to the amino acid sequence being linked on the N-terminal side of the base domain, and a region including: a peptide comprising EIPFYGKAI (SEQ. ID. No. 7) or a peptide having an amino acid sequence that has at least 90% sequence identity to the amino acid sequence; a peptide comprising KLSALGVNA (SEQ. ID. No. 9) or a peptide having an amino acid sequence that has at least 90% sequence identity to the amino acid sequence; and a peptide comprising VATDALMTGYTGDFDSVIDC (SEQ. ID. No. 10) or a peptide having an amino acid sequence that has at least 90% sequence identity to the amino acid sequence being linked on the C-terminus;

(3) the base domain is a polypeptide comprising an amino acid sequence of SEQ. ID. No. 18 or a polypeptide having an amino acid sequence that has at least 90% sequence identity to the amino acid sequence, a region including a peptide comprising QSFLATCINGVCWTVYHGAG (SEQ. ID. No. 4) or a peptide having an amino acid sequence that has at least 90% sequence identity to the amino acid sequence being linked on the N-terminal side of the base domain, and a region including a peptide comprising TPAETSVRLRAYLNTPG (SEQ. ID. No. 15) or a peptide having an amino acid sequence that has at least 90% sequence identity to the amino acid sequence being linked on the C-terminal side; or (4) the base domain includes a polypeptide comprising an amino acid sequence of SEQ. ID. No. 19 or a polypeptide having an amino acid sequence that has at least 90% sequence identity to the amino acid sequence, a region including a polypeptide comprising an amino acid sequence of SEQ. ID. No. 16 or a polypeptide having an amino acid sequence that has at least 90% sequence identity to the amino acid sequence, a peptide comprising EIPFYGKAI (SEQ. ID. No. 7) or a peptide having an amino acid sequence that has at least 90% sequence identity to the amino acid sequence, a peptide comprising KLSALGVNA (SEQ. ID. No. 9) or a peptide having an amino acid sequence that has at least 90% sequence identity to the amino acid, and a peptide comprising VATDALMTGYTGDFDSVIDC (SEQ. ID. No. 10) or a peptide having an amino acid sequence that has at least 90% sequence identity to the amino acid being linked on the C-terminal side.

In one embodiment, the gene for expressing an immunogenic polypeptide on a cell surface of a *bifidobacterium* further includes a gene encoding a *bifidobacterium*-derived GNB/LNB substrate-binding membrane protein, wherein the gene encoding the immunogenic polypeptide is positioned 3' to the *bifidobacterium*-derived GNB/LNB substrate-binding membrane protein.

The present invention also provides a plasmid for gene expression, comprising the gene for expressing an immunogenic polypeptide on a cell surface of a *bifidobacterium*, in an expressible form.

The present invention further provides a transformed *bifidobacterium*, harboring the plasmid to present the immunogenic polypeptide on a cell surface.

The present invention further provides a transformed *bifidobacterium*, comprising, in a genome, the gene for expressing an immunogenic polypeptide on a cell surface of a *bifidobacterium*, in an expressible form to present the immunogenic polypeptide on a cell surface.

The present invention also provides a vaccine composition for hepatitis C, comprising the transformed *bifidobacterium* presenting the hepatitis C virus antigenic polypeptide on a cell surface.

In one embodiment, the vaccine composition is an oral vaccine.

The present invention further provides a method for designing an immunogenic polypeptide for expression on a cell surface of a *bifidobacterium*, the method comprising the steps of selecting a base domain holding a conformation and having a cell sectional capacity and at least one antigenic peptide; and designing a synthetic polypeptide in which the at least one antigenic peptide is linked on either one of an N-terminal side and a C-terminal side of the base domain.

In one embodiment, the base domain includes at least one CD4 epitope or CD8 epitope, or both.

The present invention also provides a transformed *bifidobacterium* that expresses a polypeptide, which is specifically expressed on a cell surface of a cancer cell, on a cell surface.

In one embodiment, the transformed *bifidobacterium* further includes a gene encoding a *bifidobacterium*-derived GNB/LNB substrate-binding membrane protein.

The present invention also provides a cancer vaccine comprising the transformed *bifidobacterium*.

Effects of Invention

According to the present invention, an immunogenic polypeptide can be expressed and presented on the cell surface of bifidobacteria. Furthermore, according to the present invention, for example, hepatitis C virus antigen specific immunity can be induced in an animal orally administered with bifidobacteria presenting an immunogenic hepatitis C virus antigenic polypeptide on the cell surface, which can be utilized as a vaccine composition (oral vaccine, for example).

BRIEF DESCRIPTION OF DRAWINGS

FIG. 1 shows an amino acid sequence including a NS3 protein full-length region of a HCV type 1b polypeptide (GenBank: BAA08120.1).

FIG. 2 shows amino acid sequences 1 and 2, which are examples of a synthetic NS3 polypeptide in which NS3-derived antigenic peptides are linked to the N-terminus and C-terminus of a base domain that is based on a linker region of NS3 and an N-terminal β-α-β domain of the HCV type 1b polypeptide.

FIG. 3 is a photograph showing the result of Western blotting relating to the expression of the synthetic NS3 protein in wild-type *Bifidobacterium longum* 245, *Bifidobacterium longum* 2164, and *Bifidobacterium longum* 2165.

FIG. 8 shows an amino acid sequence, which is an example of a synthetic NS3 polypeptide in which NS3-derived antigenic peptides are linked to the N-terminus and C-terminus of the base domain that is based on an α-helical domain of NS3 of the HCV type 1b polypeptide.

FIG. 9 shows an amino acid sequence, which is an example of a synthetic NS3 polypeptide in which NS3-derived antigenic peptides are linked to the N-terminus and C-terminus of the base domain that is based on the C-terminal β-α-β domain of NS3 of the HCV type 1b polypeptide.

FIG. 10 shows an amino acid sequence, which is an example of a synthetic NS3 polypeptide in which NS3-derived antigenic peptides are linked to the C-terminus of the base domain that is based on a NS3 β-barrel domain in which a part of the NS4A region of the HCV type 1b polypeptide is linked to its N-terminus.

FIG. 11 shows the construction of a plasmid pBApo-CMVNeo/NS3/4A.

FIG. 12 shows detection of a NS3/4A fragment by RT-PCR.

Figure 4:
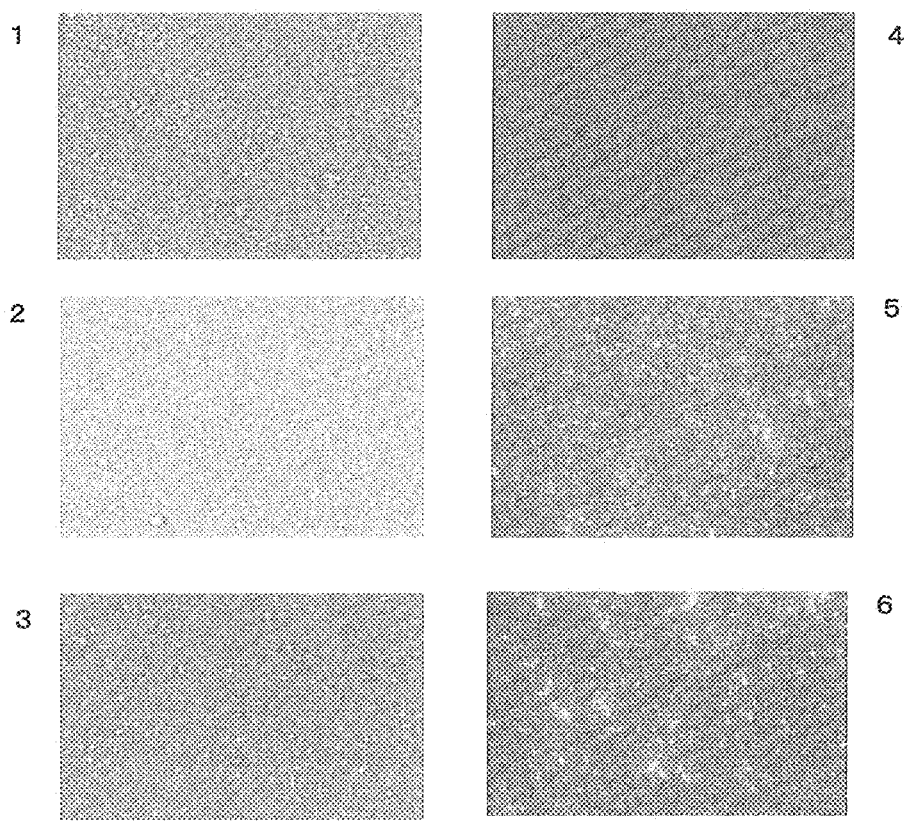
FIG. 4 shows bright-field photomicrographs (1 to 3) and fluorescent photomicrographs (4 to 6) of *Bifidobacterium longum* 245 (1, 4), *Bifidobacterium longum* 2164 (2, 5), and *Bifidobacterium longum* 2165 (3, 6).

MODE FOR CARRYING OUT THE INVENTION (Bifidobacteria)

In the present invention, "bifidobacteria" refer to microorganisms belonging to the genus *Bifidobacterium*. Examples of the bifidobacteria include *Bifidobacterium adolescentis*, *B. angulatum*, *B. animalis* subsp. *animalis*, *B. animalis* subsp. *lactis*, *B. asteroides*, *B. bifidum*, *B. boum*, *B. breve*, *B. catenubtum*, *B. choerinum*, *B. coryneforme*, *B. cuniculi*, *B. denticolens*, *B. dentium*, *B. gallicum*, *B. gallinarum*, *B. globosum*, *B. indicum*, *B. infantis*, *B. inopinatum*, *B. lactis*, *B. longum*, *B. magnum*, *B. merycicum*, *B. minimum*, *B. parvulorum*, *B. pseudocatenulatum*, *B. pseudolongum* subsp. *globosum*, *B. pseudolongum* subsp. *pseudolongum*, *B. pullorum*, *B. ruminale*, *B. ruminantium*, *B. saeculare*, *B. scardovii*; *B. subtile*, *B. suis*, *B. thermacidophilum*, and *B. thermophilum*. Furthermore, resistant strains or mutant strains of these bifidobacteria may be used.

These bacterial strains are commercially available or readily available from depositories. Examples of the bacterial strains include *B. longum* JCM1217 (ATCC15707), *B. bifidum* ATCC11863 and *B. longum* 105-A strain (Biosci. Biotechnol. Biochem., vol. 61, p. 1211-1212, 1997).

(GNB/LNB Substrate-Binding Membrane Protein)

The GNB/LNB substrate-binding membrane protein (GLBP) is a membrane protein belonging to the ATP-Binding Cassette (ABC) protein family, which transports lacto-N-biose (i.e., N-acetyl-3-O-(13-D-galactopyranosyl)-D-glucosamine) and galacto-N-biose (i.e., N-acetyl-3-O-(13-D-galactopyranosyl)-D-galactosamine) of a *bifidobacterium*. ABC proteins are important membrane proteins that actively transport specific substances on the cell membranes of any organisms using an energy called adenosine triphosphate (ATP), and various ABC proteins are present on the cell membranes. Therefore, if an appropriate promoter is used, GLBP, which is an ABC protein, is ubiquitously expressed in bacteria belonging to the genus *Bifidobacterium* (bifidobacteria), which have a cellular function for expressing GLBP on the cell surface. For example, GLBP derived from the *Bifidobacterium longum* JCM1217 (ATCC15707) strain has an amino acid sequence of SEQ. ID. No. 2 in the sequence listing (the corresponding base sequence is shown by SEQ. ID. No. 1).

The structure of GLBP is not limited to the structure of naturally occurring GLBP, and amino acids constituting the GLBP may include one or more (for example, one or several) of substitutions, insertions or deletions, so long as the GLBP has an ability of being expressed on the cell surface of a *bifidobacterium*.

(Immunogenic polypeptide)

In the present invention, an immunogenic polypeptide to be expressed on the cell surface of *bifidobacterium* is comprised of a base domain that holds a conformation and has a cell secretional capacity and at least one antigenic peptide. The at least one antigenic peptide is linked on any of the N-terminal side and the C-terminal side of the base domain.

"Immunogenicity" means that an antigen can induce a T lymphocyte response (CD4+ and/or CD8+) unique to the antigen.

As the base domain, any region that holds a conformation (which forms a secondary structure (such as β-sheet or α-helix) in a crystal structure, for example) and has a cell secretional capacity (which does not include consecutive basic amino acid residues, or is modified not to include consecutive basic amino acid residues, for example) can be used. Examples of a domain that holds a conformation include α-β-α domain, β-barrel domain, and α-helix domain. The conformation of a protein can be determined by X-ray crystallography that is commonly used by a person skilled in the art, for example, and the base domain can be selected based on known or estimated X-ray crystallographic information (Protein Data Bank (http://www.rcsb.org/pdb/home/home.do); Bioinformatics, vol. 22, p. 195-201, 2006; and Protein Science, vol. 2, p. 305-314, 1993, for example). The base domain preferably includes at least one CD4 epitope and/or CD8 epitope in the domain.

"Cell secretional capacity" means that a polypeptide (protein) has the capacity of being extracellularly secreted by a transport apparatus on the cell membrane of bifidobacteria. In order to have the cell secretional capacity, it is desirable that the region does not include two or more consecutive basic amino acids (histidine, lysine, and arginine) (in other words, an amino acid other than basic amino acids exists before and after a basic amino acid in the region). If two or more consecutive basic amino acids is included in a region, the region can be modified by substitution with another amino acid as described below.

"Antigenic peptide" means any peptide that exhibits antigenicity. An antigenicity exhibiting peptide encompasses a CD4 epitope (helper T lymphocyte recognition epitope) and a CD8 epitope (cytotoxic T lymphocyte recognition epitope). Such a peptide can be determined by epitope mapping commonly used by a person skilled in the art, for example, and can be obtained.

An antigenic peptide may have one or more (one or several, for example) substitutions, insertions, and/or deletions of amino acids constituting the epitope as long as the antigenic peptide has the capacity of exhibiting desired properties (in particular, antigenicity). For example, the antigenic peptide may include further addition of an amino acid sequence comprised of one or more amino acids (preferably, 1 to 5 amino acids) derived from a region extending from the N-terminus and/or C-terminus of an epitope in the protein from which the epitope is derived (that is, in which the epitope originally exists); deletion of one or more amino acids (preferably, three or less amino acids) from either one of the N-terminus or C-terminus of the amino acid sequence of the epitope; or substitution of one or more amino acids (preferably, three or less amino acids) in the amino acid sequence of the epitope; or a combination thereof.

If two or more identical or different consecutive basic amino acids (histidine, lysine, and arginine) exists in the amino acid sequence of the corresponding conformation region of the original protein from which the base domain is derived, any of the consecutive basic amino acids can be substituted by another amino acid such that desirable effects (conformation and secretional capacity of the base domain) are exhibited. There is no need to substitute all of the two or more consecutive basic amino acids, and it is sufficient that the remaining consecutive basic amino acids are substituted except for one basic amino acid among them. A substituted amino acid may be any amino acid other than basic amino acids, and can be for example, alanine, methionine, glutamic acid, glutamine, and leucine; preferably glutamic acid, glutamine, and leucine; and more preferably the consecutive basic amino acids can be substituted such that glutamine and leucine are arranged in this order. The base domain may include one or more (one or several, for example) substitutions, insertions, and/or deletions of amino acids as long as the base domain can hold its conformation and has a cell secretional capacity. Also, a plurality of types of base domains may be used. The base domain may have further addition of an amino acid sequence comprised of one or more amino acids (preferably, 1 to 5 amino acids) derived from an N-terminal region and/or a C-terminal region of the base domain in the protein from which the base domain is derived (that is, in which the base domain originally exists); deletion of one or more amino acids (preferably, 3 or less amino acids) from either one of the N-terminus or C-terminus of the amino acid sequence of the base domain; or substitution of one or more amino acids (preferably, 3 or less amino acids) in the amino acid sequence of the base domain; or a combination thereof.

A variant having substitution, insertion, and/or deletion of one or more amino acids is preferably a conservatively modified variant. "Conservatively modified variant" is applied to both amino acid and nucleic acid sequence. With regard to a specific nucleic acid sequence, the conservatively modified variant encompasses a nucleic acid sequence encoding the same amino acid sequence and an amino acid sequence having one or more conservative substitutions. Examples of the conservative substitution include replacement of one amino acid among the following groups with another amino acid in the same group:

(1) Hydrophobic: isoleucine, valine, leucine, phenylalanine, methionine, alanine, tryptophan, and glycine;
(2) Neutrophilic: cysteine, serine, threonine, asparagine, glutamine, and tyrosine;
(3) Acidic: aspartic acid and glutamic acid;
(4) Basic: histidine, lysine, and arginine;
(5) Residue affecting chain orientation: glycine and proline;
(6) Aromatic: tryptophan, tyrosine, and phenylalanine; and
(7) Small amino acid: glycine, alanine, and serine.

The amino acid sequence of such a variant has a sequence identity % of at least 90%, more preferably at least 95%, and even more preferably at least 99%. The terms "sequence identity percent" and "sequence identity %" mean the percentage of sequence identity found by a comparison or alignment of two or more amino acid or nucleic acid sequences. The identity percent can be determined by a direct comparison of sequence information between two molecules through aligning sequences, calculating an accurate number of matches between the two aligned sequences, dividing the calculated number of matches by the length of a shorter sequence, and multiplying the result by 100. The algorithm for calculating the percent identity is the Smith-Waterman homology search algorithm (Proteins, vol. 48, p. 367-376, 2002; Bioinformatics, vol. 17, p. 327-337, 2001, for example).

The antigenic peptide can be expressed and presented on the *bifidobacterium* cell surface in combination with the base domain to exhibit immunogenicity. At least one antigenic peptide can be added to one or both of the N-terminal side and the C-terminal side of the base domain. For example, if more than one antigenic peptides are added, each of the antigenic peptides can be added to one or both sides of the base domain. If the base domain has an epitope region, the antigenic peptide to be linked thereto can be selected such that the immunogenicity can be exhibited by the epitope of the antigenic peptide and the epitope of the base domain, for example.

Hereinafter, a hepatitis C virus (HCV) immunogenic polypeptide will be described as an example.

FIG. 1 shows an amino acid sequence (SEQ. ID. No. 3) including a NS3 protein full-length region of HCV type 1b polypeptide (GenBank: BAA08120.1). The amino acid sequence from position 1027 to position 1657 in FIG. 1 corresponds to a full-length NS3 (herein, a position number of amino acid is based on the position in the full length of the HCV type 1b polypeptide, unless otherwise stated). The NS3 protein is formed by a β-barrel domain (position 1027 to position 1195), a linker region (position 1196 to position 1215), two β-α-β domains (N-terminal domain: position 1216 to position 1350, and C-terminal domain: position 1351 to position 1509), and an α-helical domain (position 1510 to position 1657) (Non-Patent Document 1).

FIG. 1 also shows the distribution of the CD8 epitopes (shown with a single underline in FIG. 1) and the CD4 epitopes (shown with a double underline in FIG. 1) in the NS3 protein region. In FIG. 1, the CD8 epitopes are:
  position 1067 to position 1086: QSFLATCINGVCWT-VYHGAG (CD8 Epitope 1: SEQ. ID. No. 4);
  position 1169 to position 1177: LLCPSGHVV (CD8 Epitope 2: SEQ. ID. No. 5);
  position 1291 to position 1298: ITYSTYGK (CD8 Epitope 3: SEQ. ID. No. 6);
  position 1372 to position 1380: EIPFYGKAI (CD8 Epitope 4: SEQ. ID. No. 7);
  position 1391 to position 1399: LIFCHSKKK (CD8 Epitope 5: SEQ. ID. No. 8);
  position 1406 to position 1414: KLSALGVNA (CD8 Epitope 6: SEQ. ID. No. 9);
  position 1435 to position 1454: VATDALMTGYTGD-FDSVIDC (CD8 Epitope 7: SEQ. ID. No. 10); and
  position 1629 to position 1637: GAVQNEVTL (CD8 Epitope 8: SEQ. ID. No. 11), and the CD4 epitopes are:
  position 1130 to position 1149: LYLVTRHADVIPVR-RRGDSR (CD4 Epitope 1: SEQ. ID. No. 12);
  position 1202 to position 1220: ETTMRSPVFTDNSTP-PAVP (CD4 Epitope 2: SEQ. ID. No. 13);
  position 1303 to position 1330: GGCSGGAYDIIIC-DECHSTDSTSILGIG (CD4 Epitope 3: SEQ. ID. No. 14); and
  position 1531 to position 1547: TPAETSVRLRAY-LNTPG (CD4 Epitope 4: SEQ. ID. No. 15).

Examples of the base domain of the hepatitis C virus (HCV) immunogenic polypeptide include the following:

(1) Base domain based on the linker region (position 1196 to position 1215) and the N-terminal β-α-β domain (position 1216 to position 1350) of the NS3 protein in the HCV type 1b antigenic polypeptide (FIG. 2) VPVESMETTMR-SPVFTDNSTPPAVPQSFQVAHLHAPTGSGKSTKV-PAAYAAQGY KVLVLNPSVAATLGFGAYMSKAHGVD-PNIRTGVRTITTGAPITYSTYGKFLADGG CSGGAYDIIICDECHSTDSTSILGIGTVLDQAETAGAR-LVVLATAT (SEQ. ID. No. 16);

(2) Base domain based on the α-helical domain (position 1510 to position 1657) of the NS3 protein in the HCV type 1b antigenic polypeptide (FIG. 8) GMFDSSVLCECYDAG-CAWYELTPAETSVRLRAYLNTPGLPVCQDHLEF-WESVF TGLTHIDAHFLSQTKQAGDNFPYLVAYQATV-CARAKAPPPSWDQMWKCLIRLK PTLHGPTPLLYRLGAVQNEVTLTHPITKFIMACM-SADLEVVT (SEQ. ID. No. 17);

(3) Base domain based on the C-terminal β-α-β domain (position 1510 to position 1657) of the NS3 protein in the HCV type 1b polypeptide (where three amino acids from position 1351 to position 1353 are deleted, and two Ks (lysines) at positions 1398 and 1399 of the downstream β-α-β domain of NS3 are substituted by Q (glutamine: position 1398) and L (leucine: position 1399)) (FIG. 9) SVTVPHPNIEEVALSNTGEIPFYGKAIPLEAIKG-GRHLIFCHSKQLCDELAAKLSA LGVNAVAYYRGLD-VSIIPTSGDVVVVATDALMTGYTGDFDSVID-CNTCVTQTVDF SLDPTFTIETTTVPQDAVSRSQMQGRTGRGRGGIYR-FVTPGERPS (SEQ. ID. No. 18); and (4) Base domain based on the β-barrel domain (position 1027 to position 1195) of the NS3 protein in which a part (position 1677 to position 1690, for example) of the NS4A region is linked to its N-terminus (where two amino acids at positions 1027 and 1028 and an amino acid at position 1195 are deleted, and two Rs (arginines) at positions 1144 and 1145 are substituted by Q (glutamine: position 1144) and L (leucine: position 1145)) (FIG. 10) TGSVVIVGRIILSGI-TAYSQQTRGLLGCIITSLTGRDKNQVEGEVQV-VSTATQSFLA TCINGVCWTVYHGAGSKTLAGPKG-PITQMYTNVDQDLVGWPAPPGARSMTPCT CGSSDLYLVTRHADVIPVRQLGDSRGSLLSPRPI-SYLKGSSGGPLLCPSGHVVGIF RAAVCTRGVAKAVD (SEQ. ID. No. 19: TGSVVIVGRIILSG (SEQ. ID. No. 20) in FIG. 10 is derived from the NS4A region).

The hepatitis C virus (HCV) immunogenic polypeptide expressed on the cell surface of *bifidobacterium* can include one or more of Base Domains (1) to (4) described above as the base domain. For example, Base Domains (1) to (4) can be used alone or in combination with one or more of other Base Domains.

Base domain (1) includes ETTMRSPVFTDNSTPPAVP (position 1202 to position 1220, CD4 Epitope 2: SEQ. ID. No. 13), ITYSTYGK (position 1291 to position 1298, CD8 Epitope 3: SEQ. ID. No. 6), and GGCSGGAYDIIICDECH-STDSTSILGIG (position 1303 to position 1330, CD4 Epitope 3: SEQ. ID. No. 14), for example. Base domain (2) includes TPAETSVRLRAYLNTPG (position 1531 to position 1547, CD4 Epitope 4: SEQ. ID. No. 15) and GAVQ-NEVTL (position 1629 to position 1637, CD8 Epitope 8: SEQ. ID. No. 11), for example. Base domain (3) includes EIPFYGKAI (position 1372 to position 1380, CD8 Epitope 4: SEQ. ID. No. 7), LIFCHSKQL (position 1391 to position 1399, KK of CD8 Epitope 5 are substituted with QL: SEQ. ID. No. 21), KLSALGVNA (position 1406 to position 1414, CD8 Epitope 6: SEQ. ID. No. 9), and VATDALMTGYT- GDFDSVIDC (position 1435 to position 1454, CD8 Epitope 7: SEQ. ID. No. 10), for example.

Base domain (4) includes QSFLATCINGVCWTVYHGAG (position 1067 to position 1086, CD8 Epitope 1: SEQ. ID. No. 4), LYLVTRHADVIPVRQLGDSR (position 1130 to position 1149, RR of CD4 Epitope 1 are substituted with QL: SEQ. ID. No. 22), and LLCPSGHVV (position 1169 to position 1177, CD8 Epitope 2: SEQ. ID. No. 5), for example.

At least one of HCV antigenic peptides are linked on the N-terminal side and/or the C-terminal side of the base domain. The antigenic peptide includes a peptide including an amino acid sequence selected from the group consisting of the following amino acid sequences:

QSFLATCINGVCWTVYHGAG; (SEQ. ID. No. 4)

LYLVTRHADVIPVRRRGDSR; (SEQ. ID. No. 12)

LLCPSGHVV; (SEQ. ID. No. 5)

ETTMRSPVFTDNSTPPAVP; (SEQ. ID. No. 13)

ITYSTYGK; (SEQ. ID. No. 6)

GGCSGGAYDIIICDECHSTDSTSILGIG; (SEQ. ID. No. 14)

EIPFYGKAI; (SEQ. ID. No. 7)

LIFCHSKKK; (SEQ. ID. No. 8)

KLSALGVNA; (SEQ. ID. No. 9)

VATDALMTGYTGDFDSVIDC; (SEQ. ID. No. 10)

TPAETSVRLRAYLNTPG; and (SEQ. ID. No. 15)

GAVQNEVTL. (SEQ. ID. No. 11)

The above-described peptides are CD4 epitopes or CD8 epitopes derived from the NS3 protein in the HCV type 1b antigenic polypeptide. Although the CD4 epitopes and the CD8 epitopes are arranged as shown in FIG. 1, there is no particular limitation on the type and the number of epitopes of the antigenic peptide to be linked to the base domain, the position at which an epitope is linked to the base domain (whether on the N-terminal side or C-terminal side), and the order of linkage when a plurality of epitopes are linked to a terminus. A region including an epitope, such as Base Domains (1) to (4) described above, can also be used as the antigenic peptide. The antigenic peptide may be redundant with the epitope arranged in the base domain. The antigenic peptide to be linked thereto can be selected such that the immunogenicity can be exhibited by the epitope of the antigenic peptide and the epitope in the base domain, for example.

The above-described CD4 epitope or CD8 epitope in the antigenic peptide may have one or more (one or several, for example) substitutions, insertions, and/or deletions of amino acids as long as the epitope has the capacity of exhibiting antigenicity. For example, the antigenic peptide may include further addition of an amino acid sequence comprised of one or more amino acids (preferably, 1 to 5 amino acids) derived from a region extending from the N-terminus and/or C-terminus of the epitope in the NS3 protein from which the epitope is derived (that is, in which the epitope originally exists); deletion of one or more amino acids (preferably, 3 or less amino acids) from either one of the N-terminus or C-terminus of the amino acid sequence of the epitope; or substitution of one or more amino acids (preferably, 3 or less amino acids) of the amino acid sequence in the epitope; or a combination thereof. An antigenic peptide that is used as HCV antigenic polypeptides for *bifidobacterium* cell surface expression may have an amino acid sequence having at least 90%, more preferably at least 95%, and even more preferably at least 99% sequence identity to the amino acid sequence of the above-described CD4 epitope or CD8 epitope peptides as long as the peptide has the capacity of exhibiting the antigenicity.

If a corresponding region of the original NS3 protein which is selected as the base domain includes two or more consecutive basic amino acids (histidine, lysine, and arginine), the consecutive basic amino acids may be substituted by another amino acid such that desirable effects (conformation and cell secretional capacity of the base domain) are exerted. A substituted amino acid may be any amino acid other than the basic amino acids, and can be for example, alanine, methionine, glutamic acid, glutamine, and leucine; preferably glutamic acid, glutamine, and leucine; and the consecutive basic amino acids can be more preferably substituted such that glutamine and leucine are arranged in this order.

The base domain may have one or more (one or several, for example) substitutions, insertions, or deletions of amino acids as long as the base domain can hold its conformation and has a cell secretional capacity for cell surface expression.

The base domain may include further addition of an amino acid sequence consisting of one or more amino acids (preferably, 1 to 5 amino acids) derived from a region extending from the N-terminus and/or C-terminus of a region corresponding to the base domain in the NS3 protein from which the base domain is derived (that is, in which the base domain originally exists); deletion of one or more amino acids (preferably, 3 or less amino acids) from either one of the N-terminus or C-terminus of the amino acid sequence of the base domain; or substitution of one or more amino acids (preferably, 3 or less amino acids) in the amino acid sequence of the base domain; or a combination thereof. The base domain that is used in the HCV antigenic polypeptide for *bifidobacterium* cell surface expression may have an amino acid sequence having at least 90%, more preferably at least 95%, and even more preferably at least 99% sequence identity to the amino acid sequences of Base Domains (1) to (4) described above.

In the case of Base Domain (1), preferably, a region including QSFLATCINGVCWTVYHGAG (position 1067 to position 1086, CD8 Epitope 1: SEQ. ID. No. 4) can be linked on the N-terminal side of the base domain, and a region including at least one of EIPFYGKAI (position 1372 to position 1380, CD8 Epitope 4: SEQ. ID. No. 7), KLSALGVNA (position 1406 to position 1414, CD8 Epitope 6: SEQ. ID. No. 9), and VATDALMTGYTGDFDSVIDC (position 1435 to position 1454, CD8 Epitope 7: SEQ. ID. No. 10) in a random order, more preferably a region including EIPFYGKAI (position 1372 to position 1380, CD8 Epitope 4; SEQ. ID. No. 7), or a region including EIPFYGKAI (position 1372 to position 1380, CD8 Epitope 4: SEQ. ID.

No. 7), KLSALGVNA (position 1406 to position 1414, CD8 Epitope 6: SEQ. ID. No. 9), and VATDALMTGYTGDFDSVIDC (position 1435 to position 1454, CD8 Epitope 7: SEQ. ID. No. 10) (preferably, in this order) can be linked on the C-terminal side (the region may include a peptide having an amino acid sequence having at least 90%, more preferably at least 95%, and even more preferably at least 99% sequence identity to the amino acid sequence specified by the indicated SEQ. ID. No. as long as the peptide has the capacity of exhibiting antigenicity). Examples of synthetic protein in the case of Base Domain (1) are as shown by Amino Acid Sequences 1 and 2 of FIG. 2 (in FIG. 2, the sequence of the base domain is indicated by capital letters, the sequence of the antigenic peptide region is indicated by small letters, and the CD8 epitope and the CD4 epitope are respectively indicated using a single underline and a double underline).

In the case of Base Domain (2), preferably, a region including QSFLATCINGVCWTVYHGAG (position 1067 to position 1086, CD8 Epitope 1: SEQ. ID. No. 4) can be linked on the N-terminal side of the base domain. A region including at least one of EIPFYGKAI (position 1372 to position 1380, CD8 Epitope 4: SEQ. ID. No. 7), KLSALGVNA (position 1406 to position 1414, CD8 Epitope 6: SEQ. ID. No. 9), and VATDALMTGYTGDFDSVIDC (position 1435 to position 1454, CD8 Epitope 7: SEQ. ID. No. 10) in a random order, and more preferably, a region including EIPFYGKAI (position 1372 to position 1380, CD8 Epitope 4: SEQ. ID. No. 7), KLSALGVNA (position 1406 to position 1414, CD8 Epitope 6: SEQ. ID. No. 9), and VATDALMTGYTGDFDSVIDC (position 1435 to position 1454, CD8 Epitope 7: SEQ. ID. No. 10) (preferably, in this order) can be linked on the C-terminal side (the region may include a peptide having an amino acid sequence having at least 90%, more preferably at least 95%, and even more preferably at least 99% sequence identity to the amino acid sequence specified by the indicated SEQ. ID. No. as long as the peptide has the capacity of exhibiting antigenicity). Examples of the synthetic protein in the case of Base Domain (2) are as shown by the amino acid sequence of FIG. 8 (in FIG. 8, the sequence of the base domain is indicated by capital letters, the sequence of the antigenic peptide region is indicated by small letters, and the CD8 epitope and the CD4 epitope are respectively indicated using a single underline and a double underline).

In the case of Base Domain (3), preferably, a region including QSFLATCINGVCWTVYHGAG (position 1067 to position 1086, CD8 Epitope 1: SEQ. ID. No. 4) can be linked on the N-terminal side of the base domain. A region including TPAETSVRLRAYLNTPG (position 1531 to position 1547, CD4 Epitope 4: SEQ. ID. No. 15) can be linked on the C-terminal side (the region may include a peptide having an amino acid sequence having at least 90%, more preferably at least 95%, and even more preferably at least 99% sequence identity to the amino acid sequence specified by the indicated SEQ. ID. No. as long as the peptide has the capacity of exhibiting antigenicity). Examples of the synthetic protein in the case of Base Domain (3) are as shown by the amino acid sequence of FIG. 9 (in FIG. 9, the sequence of the base domain is indicated by capital letters, the sequence of the antigenic peptide region is indicated by small letters, and the CD8 epitope and the CD4 epitope are respectively indicated using a single underline and a double underline; and a boldfaced "QL" indicates substituted amino acids).

In the case of Base Domain (4), preferably, without linking an antigenic peptide on the N-terminal side of the base domain, a region including Base Domain (1) including ETTMRSPVFTDNSTPPAVP (position 1202 to position 1220, CD4 Epitope 2; SEQ. ID. No. 13), ITYSTYGK (position 1291 to position 1298, CD8 Epitope 3; SEQ. ID. No. 6), and GGCSGGAYDIIICDECHSTDSTSILGIG (position 1303 to position 1330, CD4 Epitope 3; SEQ. ID. No. 14) (or having an amino acid sequence having at least 90%, more preferably at least 95%, and even more preferably at least 99% sequence identity to the amino acid sequence of Base Domain (1) described above as long as the domain can hold its conformation and has a cell secretional capacity for cell surface expression) is linked on the C-terminal side, and a region including at least any one of EIPFYGKAI (position 1372 to position 1380, CD8 Epitope 4; SEQ. ID. No. 7), KLSALGVNA (position 1406 to position 1414, CD8 Epitope 6; SEQ. ID. No. 9), and VATDALMTGYTGDFDSVIDC (position 1435 to position 1454, CD8 Epitope 7; SEQ. ID. No. 10) in a random order, and preferably a region including EIPFYGKAI (position 1372 to position 1380, CD8 Epitope 4; SEQ. ID. No. 7), KLSALGVNA (position 1406 to position 1414, CD8 Epitope 6; SEQ. ID. No. 9), and VATDALMTGYTGDFDSVIDC (position 1435 to position 1454, CD8 Epitope 7; SEQ. ID. No. 10) (preferably, in this order) can be further linked on the C-terminal side (the region may include a peptide having an amino acid sequence having at least 90%, more preferably at least 95%, and even more preferably at least 99% sequence identity to the amino acid sequence specified by a SEQ. ID. No. as long as the peptide has the capacity of exhibiting antigenicity). Examples of the synthetic protein in the case of Base Domain (4) are as shown by the amino acid sequence of FIG. 10 (in FIG. 10, the sequence of the base domain is indicated by capital letters, the sequence of the antigenic peptide region is indicated by small letters, and the CD8 epitope and the CD4 epitope are respectively indicated using a single underline and a double underline; and a boldfaced "QL" indicates substituted amino acids).

(Fusion Protein Presented on Cell Surface of *Bifidobacterium*)

In the present invention, an immunogenic polypeptide that is to be expressed and presented on the cell surface of *bifidobacterium* is expressed as a fusion protein with GLBP. GLBP and an intended immunogenic polypeptide are linked from the N-terminus of this fusion protein in this order.

The gene to express the fusion protein includes a gene encoding the intended immunogenic polypeptide and a gene encoding GLBP (also referred to as "immunogenic polypeptide cell surface expression cassette gene").

The gene encoding the intended immunogenic polypeptide is positioned 3' to the gene encoding GLBP. The immunogenic polypeptide cell surface expression cassette gene may be a fusion gene in which the gene encoding the intended immunogenic polypeptide is ligated 3' to the gene encoding GLBP, or may include a gene encoding a linker having an appropriate length between the gene encoding GLBP and the gene encoding the intended immunogenic polypeptide.

(Preparation of Transformed *Bifidobacterium*)

Hereinafter, an example of a procedure for preparing transformed bifidobacteria that express and present an intended immunogenic polypeptide on the cell surface of bifidobacteria as a fusion protein will be described.

1. Genes Acquisition

The gene encoding GLBP and the gene encoding the intended immunogenic polypeptide can be obtained based on known gene sequence or amino acid sequence information. For example, the genes can be acquired by amplification through polymerase chain reaction (PCR) using genomic DNA or cDNA prepared from any *bifidobacterium* as a template with a pair of primers produced based on the sequence information of the structural genes of GLBP of the *bifidobacterium*. In general, there are multiple types of genetic codes for one amino acid, and therefore the gene may have a different base sequence from the base sequences that are based on a known base sequence or a known amino acid sequence.

For example, the gene encoding GLBP of *Bifidobacterium longum* (*B. longum*) can be obtained using the structural gene sequence of GLBP of *Bifidobacterium longum* described in Acta Crystallographica Section F., vol. F63, p. 751, 2007. For example, the gene can be obtained by amplification through PCR using the chromosomal DNA or cDNA of *Bifidobacterium longum* as a template with a pair of primers prepared based on the sequence information.

The gene encoding the intended immunogenic polypeptide can be obtained through determining a gene sequence encoding the intended immunogenic polypeptide from a designed amino acid sequence based on known or estimated gene sequence information, and through optimizing the determined gene sequence of the gene encoding the intended immunogenic polypeptide, taking the codon frequency of a host into consideration as required.

For example, Gene Sequences 1 and 2 respectively encoding Amino Acid Sequences 1 and 2 of FIG. 2, which are examples of the synthetic protein based on Base Domain (1), are indicated by base sequences optimized based on the codon frequency of a *bifidobacterium*. The base sequences of Gene Sequences 1 and 2 are as those shown by SEQ. ID. Nos. 25 and 27 (the corresponding amino acid sequences are respectively indicated by SEQ. ID. Nos. 26 and 28).

The base sequence of genes that encode the amino acid sequence of FIG. 8, which is an example of the synthetic protein based on Base Domain (2), and that is optimized based on the codon frequency of a *bifidobacterium* is as shown by SEQ. ID. No. 33 (the corresponding amino acid sequence is indicated by SEQ. ID. No. 34).

The base sequence of genes that encode the amino acid sequence of FIG. 9, which is an example of the synthetic protein based on Base Domain (3), and that is optimized based on the codon frequency of a *bifidobacterium* is as that shown by SEQ. ID. No. 35 (the corresponding amino acid sequence is indicated by SEQ. ID. No. 36).

The base sequence of genes that encode the amino acid sequence of FIG. 10, which is an example of the synthetic protein based on Base Domain (4), and that is optimized based on the codon frequency of a *bifidobacterium* is as that shown in SEQ. ID. No. 39 (the corresponding amino acid sequence is indicated by SEQ. ID. No. 40).

A coding gene can be obtained by, for example, a known chemical synthesis method, based on a base sequence so obtained. Examples of the chemical synthesis method include chemical synthesis with a DNA synthesizer using phosphoramidite. Furthermore, the above-mentioned gene can also be obtained by amplification of DNA through PCR by preparing primers based on base sequences in the 5' end and the 3' end of a base sequence to be obtained and using cDNA synthesized from mRNA contained in various tissues or cells of the source organism or cDNA selected from a cDNA library as a template. Furthermore, the above-mentioned gene can be obtained by colony hybridization or plaque hybridization of cDNA synthesized from mRNA contained in various tissues or cells of the source organism or the cDNA library, using a full-length or partial DNA or polynucleotide chemically synthesized based on known base sequence information as a probe.

Furthermore, the gene encoding each protein as mentioned above can also be readily obtained based on known amino acid sequence information. Examples of methods for obtaining the gene encoding each protein as mentioned above based on known amino acid sequence information include amplification of a intended gene from the above-mentioned cDNA library or the like through PCR using synthesized DNA primers having a partial base sequence of the gene encoding a known amino acid sequence, or selection by hybridization of a gene incorporated into a suitable vector with a labeled DNA fragment or synthesized DNA (probe) encoding a part or a full-length of the gene encoding each protein as mentioned above.

The gene encoding each protein as mentioned above may be a DNA that is hybridizable with a gene obtained as described above under stringent conditions. The DNA that is hybridizable under stringent conditions means a DNA obtainable by colony hybridization, plaque hybridization, southern blot hybridization, or the like using the above-mentioned DNA as a probe. Specific examples of such DNAs include a DNA that can be identified by performing hybridization at approximately 65° C. in the presence of approximately 0.7 to 1.0 M sodium chloride using a filter on which a DNA derived from a colony or a plaque is immobilized and then washing the filter using an SSC solution having an approximately 0.1 to 2-fold concentration (an SSC solution having a 1-fold concentration is composed of 150 mM sodium chloride and 15 mM sodium citrate) at approximately 65° C. Specific examples of the above-mentioned hybridizable DNA include a DNA having a homology of at least 80%, preferably a DNA having a homology of at least 90%, more preferably a DNA having a homology of at least 95% with the base sequence of the gene encoding each protein obtained based on the above-mentioned known base sequence information or amino acid sequence information.

2. Preparation of Immunogenic Polypeptide Cell Surface Expression Cassette Gene and Vector for Transforming *Bifidobacterium*

An immunogenic polypeptide cell surface expression cassette gene or recombinant DNA including the immunogenic polypeptide cell surface expression cassette gene is prepared from the genes encoding respective proteins prepared as described above. As described above, the immunogenic polypeptide cell surface expression cassette gene is prepared such that the gene encoding the intended immunogenic polypeptide is positioned 3' to the gene encoding GLBP. In the present invention, the recombinant DNA can be an expression vector or a chromosome integration vector (homologous recombination vector, for example). There is no particular limitation on plasmids used for preparation of such a vector as long as the plasmid can be expressed in *bifidobacterium*. As a plasmid derived from *bifidobacterium* pTB6, pBL67, pBL78, pNAL8H, pNAL8M, pNAC1, pBC1, pMB1, pGBL8b, or the like is used. These plasmids can also be used as a composite plasmid with a plasmid of *Escherichia coli* and examples of composite plasmid include pBLES100, pKKT427, and pRM2.

Among the above-mentioned plasmids, composite plasmids synthesized from plasmids of *Bifidobacterium longum* and plasmids of *Escherichia coli* are preferred from the viewpoint of stabile expression and easy DNA preparation for preparation of a transformant strain.

Expression vectors preferably have a selectable marker such as antibiotic resistance or amino acid auxotrophy from the viewpoint of selection of a transformant strain.

Expression vectors preferably contain a regulatory sequence for the expression of, or to be advantageous to expression of, the fusion protein of GLBP and an intended immunogenic polypeptide. Examples of regulatory sequences include promoter sequences, leader sequences, propeptide sequences, enhancer sequences, signal sequences, and terminator sequences. The origin of these regulatory sequences is not particularly limited so long as expressible in a *bifidobacterium*.

The promoter sequences are not particularly limited so long as expressible in a *bifidobacterium*. From the viewpoint of expression efficiency, the promoter sequence of a histone-like protein (HU), LDH promoter, and the like of *B. longum* are preferably used.

Expression vectors preferably have a terminator sequence from the viewpoint of improving expression efficiency. The terminator sequence of the above-mentioned HU gene is preferably used as a terminator sequence.

In addition, a leader sequence, a propeptide sequence, an enhancer sequence, a signal sequence, and the like can be arranged as required. Furthermore, a gene encoding a linker having an appropriate length may be positioned between the gene encoding GLBP and the gene encoding an intended immunogenic polypeptide.

Thus, a cloning vector is prepared by introducing regulatory sequences such as a promoter sequence and a terminator sequence and a selectable marker gene into the above-mentioned plasmid as required. Examples of the selectable marker include antibiotic resistance markers such as spectinomycin (SPr), ampicillin (Ampr), tetracycline (TETr), kanamycin (KMr), streptomycin (STr), and neomycin (NEOr); fluorescent markers such as green fluorescent protein (GFP) and red fluorescent protein (REP); and enzymes such as LacZ.

A cloning vector preferably has, for example, a linker having a multicloning site downstream of the promoter. By using such a linker, the gene (DNA) encoding the above-mentioned fusion protein is incorporated downstream of the promoter so that the fusion protein can be expressed in-frame. Representative examples of a plasmid for a cloning vector include pBLES100 and pBLEM100 (Japanese Patent No. 3642755).

For example, the HU promoter sequence, the gene encoding GLBP, and the gene encoding an intended immunogenic polypeptide obtained as described above can be incorporated in-frame into the plasmid pBLES100 to obtain a vector that expresses a fusion protein on the surface of a *bifidobacterium*. An expression vector as obtained by such a method is used for transformation of a *bifidobacterium*.

Examples of vectors for *bifidobacterium* cell surface expression also include a plasmid pJT101 (Patent Document 4 and Non-Patent Document 4) and pJW241, which is an *Escherichia coli Bifidobacterium longum* shuttle vector (Patent Document 4 and Non-Patent Document 4). The plasmid pJT101 contains a *Bifidobacterium longum* JCM 1217 (ATCC 15707)-derived GLBP gene (SEQ. ID. Nos. 1 and 2: Patent Document 4 and Non-Patent Document 4), and the gene encoding the intended immunogenic polypeptide can be incorporated in-frame downstream of the GLBP gene. Furthermore, the incorporated ligate (immunogenic polypeptide cell surface expression cassette gene) of the GLBP gene and the gene encoding the intended immunogenic polypeptide in pJT101 can be cut out, and incorporated into *Escherichia coli-Bifidobacterium longum* shuttle vector pJW241.

3. Preparation of Transformed *Bifidobacterium* Expressing Fusion Protein

Recombinant DNA such as the expression vector prepared in the above-described manner can be introduced into a host *bifidobacterium* to prepare a transformed *bifidobacterium*.

A homologous recombination method can also be used by utilizing a plasmid that is replicable within *bifidobacterium* cells to prepare a transformed bifidobacteria. According to the homologous recombination method, the immunogenic polypeptide cell surface expression cassette gene (a fusion gene in which the gene encoding the intended immunogenic polypeptide is linked 3' to the gene encoding GLBP, for example) can be inserted into *bifidobacterium* chromosome. For example, a temperature-sensitive plasmid (a plasmid that does not replicate at a high temperature (42° C. or more, for example)) having sites homologous to the *bifidobacterium* chromosomal gene can be used (Appl. Microbiol. Biotechnol., vol. 95, p. 499-509, 2012, for example). More specifically, *bifidobacterium* in which the intended gene is integrated into the chromosome through homologous recombination can be selectively cultured by inserting the immunogenic polypeptide cell surface expression cassette gene between the homologous sites of the temperature-sensitive plasmid having sites homologous to the *bifidobacterium* chromosomal gene, introducing this plasmid into *bifidobacterium*, and culturing *bifidobacterium* at a high temperature.

The expression vector for transformation or a plasmid that is replicable within *bifidobacterium* cells can be introduced using any of known methods. Specifically, examples thereof include electroporation method, calcium phosphate method, lipofection method, calcium ion method, protoplast method, microinjection method, and particle gun method. It is preferable to use the electroporation method in the present invention. It is possible to use the electroporation method under conditions of 0.5 to 20 kV/cm for 0.5 μsec to 10 msec. For example, electroporation is performed at 2 to 10 kV/cm for 50 μsec to 5 msec.

Transformants are selected using a selectable marker of the fusion protein expression vector, properties (such as temperature sensitivity) of a plasmid that is replicable within *bifidobacterium* cells, or the like. Examples of culture media for culturing transformants include culture media respectively suitable for host microorganisms, such as Glucose Blood Liver (BL) agar, de Man, Rogosa and Sharpe (MRS) agar, Gifu Anaerobic Medium (GAM) agar, improved GAM (TGAM) agar, Briggs agar, and yeast extract glucose peptone (YGP) agar. Selective pressure is applied by adding antibiotic to these culture media in accordance with a selectable marker, or lacking or adding an amino acid.

Culture is preferably performed under an anaerobic condition under which bifidobacteria can be cultured. Culture can be performed under an anaerobic condition to prevent the growth of aerobic bacteria. An example of anaerobic conditions is the condition in a sealed container in which anaerobicity sufficient to grow bifidobacteria can be maintained, for example, conditions that can be achieved in an anaerobic chamber or an anaerobic box. It is sufficient that the culture temperature is a temperature at which bifidobacteria can be cultured. The culture temperature is usually 4° C. to 45° C., preferably 15° C. to 40° C., more preferably 24° C. to 37° C.

A transformed *bifidobacterium* may be prepared in which not only a vector for surface display of a fusion protein of GLBP and a intended protein or peptide, but also a vector for surface display of a fusion protein of GLBP and a protein having an adjuvant function are simultaneously introduced.

Introduction of a gene encoding a fusion protein may be confirmed by extracting a plasmid from a transformed *bifidobacterium*, treating the plasmid with restriction enzymes, and then performing electrophoresis or directly sequencing the sequence of the restriction enzyme-treated fragment.

The expression of the fusion protein of a transformed *bifidobacterium* obtained can be confirmed, for example, using the Western blotting. First, the transformed *bifidobacterium* is lysed, for example, using a non-ionic surfactant, including polyoxyethylene sorbitan ester (Tween (registered trademark) 20, 40, 60, 65, 80, 85), and sorbitan ester (Span (registered trademark) 20, 40, 60, 65, 80, 85), and the like; then diluted with phosphate buffer, citrate buffer, borate buffer, tris(hydroxymethyl)aminomethane (Tris)-hydrochloride buffer, or the like; then subjected to electrophoresis with sodium dodecyl sulfate-polyacrylamide gel (SDS-PAGE), tris-glycine-polyacrylamide gel, or the like; then transferred to nitrocellulose membrane, polyvinylidene fluoride (PVF) membrane, or the like; and then reacted with an antibody (immunoglobulin G (IgG)) against the intended protein or peptide, and further reacted with a secondary antibody with a fluorescent label. Thereby, expression of the fusion protein can be confirmed.

In particular, the presentation of the intended immunogenic polypeptide on the *bifidobacterium* cell surface can be easily confirmed for a transformed bifidobacteria by an immune antibody method with an antibody against an intended protein or peptide and a FITC-labeled anti-IgG antibody. The immunogenicity of a *bifidobacterium* expressing the immunogenic polypeptide on the cell surface can be determined by antigen-specific IgA antibodies contained in feces (induction of topical mucosal immunity), antigen-specific IgG antibodies contained in serum (induction of systemic immunity), induced production of intracellular cytokine (Interferon γ (IFN-γ), for example) by priming, or the like.

The transformed *bifidobacterium*, in which the surface display of the intended immunogenic polypeptide has been confirmed, may be cultured, recovered, and used directly for the production of a formulation, using any methods commonly used by those skilled in the art. Alternatively, the transformed *bifidobacterium* may be used in a dry form. The transformed *bifidobacterium* can be dried by a low-temperature treatment such as freeze drying or low-temperature drying so that the *bifidobacterium* can grow when exposed to growth conditions such as those in an intestinal environment or a medium.

The transformed *bifidobacterium* may be subjected to post-treatment performed according to a known method. For example, crude purification may be performed by centrifugation or the like. The transformed *bifidobacterium* may be subjected to crude purification followed by dissolved or suspended in a solvent conventionally used in the art, such as physiological saline, phosphate-buffered saline (PBS), or lactated Ringer's solution, if desired. Also, the transformed *bifidobacterium* may be lyophilized or sprayed into the form of powders or granulates, if desired.

(Transformed *Bifidobacterium*-Containing Vaccine Composition)

A vaccine composition of the present invention contains the above-described transformed bifidobacteria as an active component. For example, in the case of transformed bifidobacteria that express an HCV immunogenic polypeptide on the cell surface, a vaccine composition of the present invention can be administered to a patient in an amount to sufficiently induce appropriate immune response to HCV infection.

The transformed bifidobacteria can be stored as frozen or lyophilized viable bacteria, suspension or cell paste of the viable bacteria, or can be stored in combination with a solid medium, gel, or liquid medium for use as a vaccine. Although there is no particular limitation on the dosage form of pharmaceutical preparation, powder, a liquid formulation in which the lyophilized powder is suspended, or an encapsulated formulation in which the lyophilized powder is enclosed are preferable. An acid-resistant capsule described in Patent Document 5 can be favorably used as the encapsulated formulation. There is no particular limitation on the administration route, and examples thereof include oral administration and parenteral administration. Oral administration or transnasal administration is preferable, and oral administration is more preferable.

Examples of a formulation suitable for oral administration include granule, fine granule, powder, syrup, solution, capsule, and suspension. Examples of a formulation suitable for parenteral administration include injection, drip infusion, inhalant, spray, suppository, percutaneous absorbing agent, and transmucosal absorbing agent.

For production of a liquid formulation for oral administration, for example, formulation additives including saccharides such as water, sucrose, sorbit, and fructose; glycols such as polyethylene glycol and propylene glycol; oils such as sesame oil, olive oil, and soybean oil; and preservatives such as p-hydroxybenzoic acid esters can be used. Furthermore, for example, excipients such as lactose, glucose, sucrose, and mannitol; disintegrating agents such as starch and sodium alginate; lubricants such as magnesium stearate and talc; binders such as polyvinyl alcohol, hydroxypropylcellulose, and gelatin; surfactants such as fatty acid esters; and plasticizers such as glycerine can be used for production of a solid formulation such as capsule, tablet, powder, or granule.

Among formulations for parenteral administration, formulations for intravascular administration such as injection and drip infusion can be preferably prepared using an aqueous vehicle that is isotonic with human blood. For example, injections can be prepared as a solution, suspension, or dispersion using an aqueous vehicle selected from a salt solution, a glucose solution, or a mixture of a salt solution and a glucose solution, together with an appropriate auxiliary agent according to a usual method. Suppositories for enteral administration can be prepared using a carrier such as cacao butter, hydrogenated oil and fat, or hydrogenated fatty acid.

Among formulations for parenteral administration, sprays can be prepared using a carrier that does not stimulate mucous membranes of the human oral cavity and respiratory tract and can promote absorption by dispersing a transformed *bifidobacterium*, an active ingredient, as fine particles. Examples of such a carrier include lactose and glycerine. Depending on the properties of a transformed *bifidobacterium* and a carrier to be used, a formulation can be prepared in the form of an aerosol, dry powder, or the like. One, or two or more formulation additives selected from, for example, diluents, flavors, preservatives, excipients, disintegrating agents, lubricants, binders, surfactants, plasticizers, and the like can be used for production of a formulation for parenteral administration.

The content of transformed bifidobacteria in the vaccine composition of the present invention can be appropriately set in accordance with the type or dosage form of pharmaceutical preparation; age, sex, weight, or disease state of subject to be administered; or method, period, time, or the like of administration or intake.

In the case where an immunogenic polypeptide is a HCV antigenic polypeptide (NS3-derived antigenic polypeptide, for example), the transformed bifidobactera of the present invention serve as an effective oral vaccine for HCV infection. The vaccine composition containing the immunogenic HCV antigenic polypeptide cell surface-expressing transformed *bifidobacterium* of the present invention can be used for both prevention and treatment of HCV infection diseases. Furthermore, the present vaccine composition can also be used in combination with an existing interferon therapy or the like.

The transformed bifidobacteria of the present invention inhibited the proliferation of tumor cells expressing NS3/4A (Example 9, FIG. 14), which is considered to indicate that the transformed bifidobacteria of the present invention functioned as a vaccine and activated the cell-mediated immunity to NS3. In other words, it is considered that as a result of oral administration of the bifidobacteria of the present invention, NS3 protein specific cytotoxic T lymphocytes (CTLs) were induced and the CTLs attacked NS3/4A expressing tumor cells, EL4s to inhibit the growth of tumors. Thus, it was confirmed that an antigenic peptide specific cell-mediated immunity was induced by an oral vaccine containing the bifidobacteria of the present invention.

The transformed bifidobacteria of the present invention can also be used for application to inhibit the growth of tumor cells. As shown in Example 9, the proliferation of NS3 protein expressing tumors was inhibited by administration of *B. longum* 2165 expressing the NS3 protein. This is thought to result from that NS3 expressed on the cell surface of *B. longum* 2165 served as an antigen to induce NS3-specific CTL, which inhibited the growth of NS3 expressing tumors.

Therefore, it is considered that a polypeptide, which is specifically expressed on the cell surface of a tumor cell but is not expressed at all in normal cells, is expressed on the cell surface of bifidobacteria, and administered to induce tumor-specific cell-mediated immunity and inhibit the growth of tumor cells.

Many antigens (cancer antigens) specifically expressed on the cell surface of a tumor cell but not expressed at all in normal cells have been reported so far, and MAGE and MART-1 in malignant melanoma, HER2/neu in breast cancer or the like, CEA in colon cancer, WT1, NY-ESO-1, and PSMA in various types of leukemia and cancer, and the like are well known, but examples of antigens are not limited thereto. Also, the cancer antigen can be identified in silico, or by wet experiment as well. Primary screening for a cancer antigen is allowed by identifying a gene estimated to be expressed on a cell surface in silico, and preparing a microarray to examine for an expression pattern. Whether the gene of a cancer antigen is expressed or not can be determined by preparing mRNA and performing RT-PCR, or preparing an antibody and performing a method known by a person skilled in the art, such as Western blotting or ELISA, to confirm the expression of a protein. Alternatively, comprehensive screening of genes specifically expressed to cancer using an microarray can be performed to identify a gene expressed on the cell surface among them.

It is considered that these cancer antigenic proteins (or polypeptides) are expressed on the cell surface of bifidobacteria, and the bacteria can be orally administered for use in the prevention and treatment of cancer as a cancer vaccine.

If the amino acid sequence of a cancer antigen is found, it is common techniques to a person skilled in the art to identify a corresponding gene in human genome, design primers, amplify the gene by PCR, and clone a gene fragment encoding the cancer antigenic polypeptide. It is also technically easy that a cloned amplification fragment is incorporated into a *bifidobacterium* cell surface expression vector to express it. Accordingly, cancer vaccines can be manufactured dependent on various cancer antigens. It is considered that administration of such a cancer vaccine allows for the prevention and treatment of cancer. The transformed bifidobacteria to be contained in the cancer vaccine of the present invention may be viable or sterile killed bacteria.

EXAMPLES

Although the present invention will be described below with reference to examples, the present invention is not limited to these examples.

Example 1: Design of HCV NS3 Polypeptide Gene for *Bifidobacterium* Cell Surface Expression Two amino acid sequences shown in FIG. 2 were designed such that NS3-derived antigenic peptides were linked to the N-terminus and the C-terminus of a base domain that was based on the NS3 linker region (position 1196 to position 1215) and the upstream β-α-β domain (position 1216 to position 1350) of the HCV type 1b polypeptide.

In Amino Acid Sequence 1 (>1 in FIG. 2: SEQ. ID. No. 23), a region including QSFLATCINGVCWTVYHGAG (position 1067 to position 1086, CD8 Epitope 1: SEQ. ID. No. 4) is linked on the N-terminal side of the base domain, and a region including EIPFYGKAI (position 1372 to position 1380, CD8 Epitope 4: SEQ. ID. No. 7), KLSALGVNA (position 1406 to position 1414, CD8 Epitope 6: SEQ. ID. No. 9), and VATDALMTGYTGDFDSVIDC (position 1435 to position 1454, CD8 Epitope 7: SEQ. ID. No. 10) in this order is linked on the C-terminal side of the base domain.

In Amino Acid Sequence 2 (>2 in FIG. 2: SEQ. ID. No. 24), a region including QSFLATCINGVCWTVYHGAG (position 1067 to position 1086, CD8 Epitope 1: SEQ. ID. No. 4) is linked on the N-terminal side of the base domain, and a region including EIPFYGKAI (position 1372 to position 1380, CD8 Epitope 4: SEQ. ID. No. 7) is linked on the C-terminal side of the base domain.

The above-described base domain is a region corresponding to position 1196 to position 1350 of the HCV type 1b antigenic polypeptide, and includes ETTMRSPVFTDNSTPPAVP (position 1202 to position 1220, CD4 Epitope 2: SEQ. ID. No. 13), ITYSTYGK (position 1291 to position 1298, CD8 Epitope 3: SEQ. ID. No. 6), and GGCSGGAYDIIICDECHSTDSTSILGIG (position 1303 to position 1330, CD4 Epitope 3: SEQ. ID. No. 14).

Example 2: Preparation of Transformed *Bifidobacterium* Expressing NS3 Protein on Cell Surface Based on Amino Acid Sequences 1 and 2 (SEQ. ID. Nos. 23 and 24 respectively) designed in Example 1, Gene Sequences 1 and 2 (SEQ. ID. Nos. 25 and 27 respectively; the corresponding amino acid sequences are respectively indicated by SEQ. ID. Nos. 26 and 28) were designed in accordance with the codon usage frequency (http://www.kazusa.or.jp/codon/) of *bifidobacterium*, and each gene fragment was totally synthesized (the former is also referred to as "long fragment" and the latter is also referred to as "short fragment") based on these pieces of gene sequence information. The total synthesis of gene fragments was consigned to GenScript Corporation. The obtained gene fragments were treated with XhoI and SalI, and inserted into the recombinant plasmid pJT101 (Patent Documents 4 and Non-Patent Document 4) that was treated with XhoI and SalI similarly. The plasmid pJT101 includes a GLBP gene (SEQ. ID. Nos. 1 and 2: Patent Document 4 and Non-Patent Document 4) from the *Bifidobacterium longum* JCM 1217 (ATCC 15707). The "long" or "short" gene fragment was ligated downstream of the GLBP gene by inserting as described above.

PCR was performed using the plasmid containing a fusion gene of "long" gene downstream of the GLBP gene as a template with a primer pair of a forward primer (5'-GGAAAACTGTCCATAGATGGCGAGGCGAACGC-CACGGT-3': SEQ. ID. No. 29) and a reverse primer (5'TTTCATCTGTGCATAGTCGACTTCAGGTGTTGCA-GTCGA-3': SEQ. ID. No. 30). On the other hand, PCR was performed using the plasmid containing a fusion gene of a "short" gene downstream of the GLBP gene as a template with a primer pair of a forward primer (5'-GGAAAACT-GTCCATAGATGGCGAGGCGAACGCCACGGT-3': SEQ. ID. No. 29) and a reverse primer (5'TTTCATCTGT-GCATATTCACAGCGGGATGGCCTTGCCGTAGA-3': SEQ. ID. No. 31). The *Escherichia coli Bifidobacterium longum* shuttle vector, pJW241 (Patent Document 4 and Non-Patent Document 4), was cleaved with NdeI, and at the site, the obtained PCR amplified fragment was ligated using an In-fusion method (Clontech Laboratories, Inc.). A cell surface expression vector containing the "long" fusion gene obtained in this manner was named pJW2165, and the cell surface expression vector containing the "short" fusion gene was named pJW2164.

The obtained surface layer expression vector, pJW2165 or pJW2164, was introduced into *Bifidobacterium longum* 105-A strain (Biosci. Biotechnol. Biochem., vol. 61, p. 1211-1212, 1997) using the electroporation method to obtain transformed *Bifidobacterium longum*. Here, the transformed *Bifidobacterium longum* into which pJW2165 was introduced was named *Bifidobacterium longum* 2165, and the transformed *Bifidobacterium longum* into which pJW2164 was introduced was named *Bifidobacterium longum* 2164. Furthermore, *Bifidobacterium longum* expressing GLBP only (*Bifidobacterium longum* 2012) was produced.

Example 3: Expression of NS3 Protein on Cell Surface of Transformed *Bifidobacterium longum*

Western blotting was performed to confirm whether a GLBP-NS3 fusion protein of a correct molecular weight was expressed in *Bifidobacterium longum* 2164 and *Bifidobacterium longum* 2165 produced according to the above-described method. After anaerobically culturing overnight using a GAM culture medium ("Nissui": Nissui Pharmaceutical Co., Ltd.), *Bifidobacterium longum* 2164 and *Bifidobacterium longum* 2165 were washed and then diluted using 1% TritonX/PBS, and a bacterial culture was subjected to polyacrylamide gel electrophoresis to separate proteins. The separated proteins were transferred to a polyvinylidene fluoride (PVDF) membrane, and blocking was performed overnight at 4° C. with 3% bovine serum albumin (BSA)/0.1% Tween20/phosphate-buffered saline (PBS). The PVDF membrane was reacted on shaking at room temperature for 1 hour using 1000-fold diluted rabbit anti-NS3 IgG (Operon Inc.) and 1000-fold diluted goat anti-rabbit IgG HRP Conjugated (Santa Cruz Biotechnology, Inc.) in this order, and the GLBP-NS3 fusion protein was detected by chemiluminescence.

The result of Western blotting is shown in FIG. 3. The lanes in FIG. 3 are as follows: M. molecular weight marker; 1. wild-type *Bifidobacterium longum* 245; 2. *Bifidobacterium longum* 2164; and 3. *Bifidobacterium longum* 2165. The molecular weight of the GLBP-NS3 fusion protein is 66 kDa in *Bifidobacterium longum* 2164 and 69 kDa in *Bifidobacterium longum* 2165, and the respective band positions are indicated by arrows in FIG. 3. The bands were confirmed at intended positions for *Bifidobacterium longum* 2164 and *Bifidobacterium longum* 2165 (lanes 2 and 3 respectively), and it was found that proteins of a molecular weight as designed were expressed.

Furthermore, in order to confirm that the NS3 protein was expressed on the cell surface of *Bifidobacterium longum* 2164 and *Bifidobacterium longum* 2165, bacterial cells were immunostained. *Bifidobacterium longum* 2164 and *Bifidobacterium longum* 2165 that were anaerobically cultured overnight using the GAM culture medium were washed, and diluted using PBS, and then blocking was performed at 37° C. for 30 minutes using 1% BSA/PBS. The bacterial cells were reacted with 50-fold diluted rabbit anti-NS3 IgG (Operon) and 1000-fold diluted Alexa. Fluor 594 goat anti-rabbit IgG (H+L) (Invitrogen) in this order at 37° C. for 1 hour respectively, and the bacterial cells was observed for fluorescent emission using a fluorescence microscope.

The result of immunostaining is shown in FIG. 4. The photographs indicate as follows: 1 and 4: *Bifidobacterium longum* 245; 2 and 5: *Bifidobacterium longum* 2164; 3 and 6: *Bifidobacterium longum* 2165; 1 to 3: bright field (400-fold); 4 to 6: under fluorescence microscope (400-fold). It was confirmed that *Bifidobacterium longum* 2164 and *Bifidobacterium longum* 2165 showed stronger fluorescence than wild-type *Bifidobacterium longum* 245, and it was found that the intended NS3 protein was expressed on the cell surface of bifidobacteria.

Example 4: Oral Administration of Transformed *Bifidobacterium longum* to Mouse

Transformed *Bifidobacterium longum* was anaerobically cultured overnight using the GAM culture medium, and was diluted using PBS to have a colony-forming unit of $5 \times 10^8$ CFU/ml. The bacterial culture was orally and intragastrically administered at 100 µl for 8-week old female BALB/C mice. The administration was performed three times per week for four weeks. As controls, PBS administration group, wild-type *Bifidobacterium longum* 245 administration group, and *Bifidobacterium longum* 2012, which expresses GLBP only, administration group were used to perform administration under the same conditions. When the day at the beginning of administration was Day 1, blood was collected from tail vein and feces were collected on Day 0, Day 14, and Day 28. On Day 29, the mice were anesthetized and euthanized by cervical dislocation and, and dissected to remove their spleens.

(4-1: Detection of HCV-NS3 Antigen-Specific Antibody by ELISA)

The NS3 antigen-specific IgA antibodies contained in the feces were detected by the enzyme-linked immunosorbent assay (ELISA). The feces were dissolved in 5% skim milk/0.1 mg/ml soybean trypsin inhibitor/2 mM phenylmethylsulfonyl fluoride/PBS to produce feces dissolving solution. A GST-NS3 antigenic peptide was coated onto 96-well immunoplate (NUNC) and blocking was performed at 37° C. for 1 hour with 5% skim milk/PBS. The solution was then reacted with the feces dissolving solution that was diluted at an appropriate concentration, and 1000-fold diluted goat anti-mouse IgA HRP (Santa Cruz) in this order, respectively, at 37° C. for 1.5 hours. Lastly, a TMB color reagent (Becton, Dickinson and Company: BD) was added to develop color for 20 minutes, and the absorbance was measured at a wavelength of 450 nm (OD 450). Also, similarly, the NS3 antigen-specific IgG antibodies contained in serum of the blood collected from the tail vein were detected by ELISA using 1000-fold diluted goat anti-mouse IgG HRP (R&D Systems Inc.).

Figure 5:
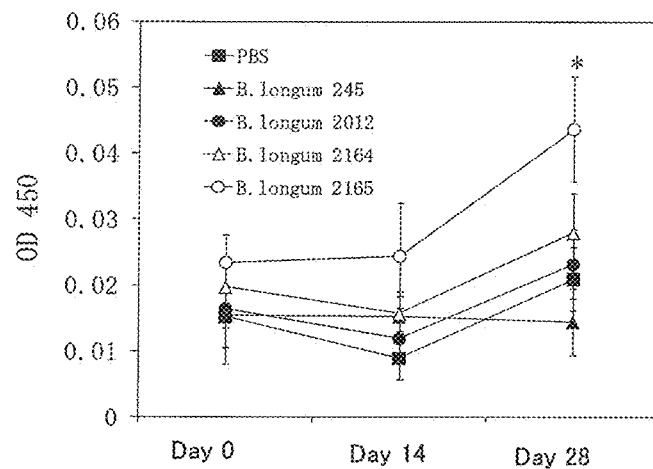
FIG. 5 is a graph showing the time cource of NS3 antigen specific IgA antibodies contained in mouse feces in various administration groups including the *Bifidobacterium longum* 2164 administration group and the *Bifidobacterium longum* 2165 administration group.

The result of ELISA to determine for the NS3 antigen-specific IgA antibodies contained in the feces is shown in FIG. 5. Marks of FIG. 5 are as follows: black square: PBS administration group; black triangle: *Bifidobacterium longum* 245 administration group; black circle: *Bifidobacterium longum* 2012 administration group; white triangle: *Bifidobacterium longum* 2164 administration group; and white circle: *Bifidobacterium longum* 2165 administration group. * indicates the presence of significant difference at $p<0.05$. With regard to the feces collected on Day 28, *Bifidobacterium longum* 2165 administration group showed significantly high absorbance (OD 450) ($p<0.05$), compared to the PBS, *Bifidobacterium longum* 245, and *Bifidobacterium longum* 2012 administration groups. On the other hand, although no significant difference was not observed, *Bifidobacterium longum* 2164 also showed a slightly high value.

Figure 6:
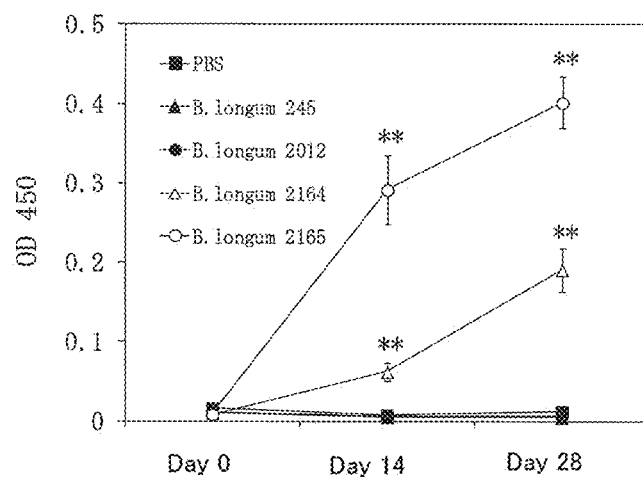
FIG. 6 is a graph showing the time cource of NS3 antigen specific IgG antibodies contained in mouse serum in various administration groups including the *Bifidobacterium longum* 2164 administration group and the *Bifidobacterium longum* 2165 administration group.

The result of ELISA to determine for the NS3 antigen-specific IgG antibodies contained in the serum is shown in FIG. 6. Marks of FIG. 6 are similar to those of FIG. 5. ** indicates the presence of significant difference at $p<0.01$. Increase in the IgG antibody amounts over days was observed for *Bifidobacterium longum* 2164 and *Bifidobacterium longum* 2165 and a significantly high value was shown on Day 14 and Day 28, compared to that of PBS, *Bifidobacterium longum* 245, and *Bifidobacterium longum* 2012 administration groups ($p<0.01$).

It was confirmed that topical mucosal immunity and systemic immune response were induced by oral administration for both *Bifidobacterium longum* 2164 and *Bifidobacterium longum* 2165.

(4-2: Cytokine Production by Spleenocytes Resulting from Antigen-Stimulation)

A spleen was subdivided using a 70 µl Cell Strainer (BD), hemolyzed using 0.83% $NH_4Cl$/PBS, and then washed. Cells were suspended using a 10% FBS/RPMI culture medium to attain $4 \times 10^5$ cells/well, and cultured for three days using a 96-well microplate while primed with 2 µg of the GST-NS3 antigenic peptide. The amount of interferon γ (IFN-γ) in supernatant of the cultured spleenocytes was measured using a Mouse IFN-γ Quantikine ELISA Kit (R&D).

Figure 7:
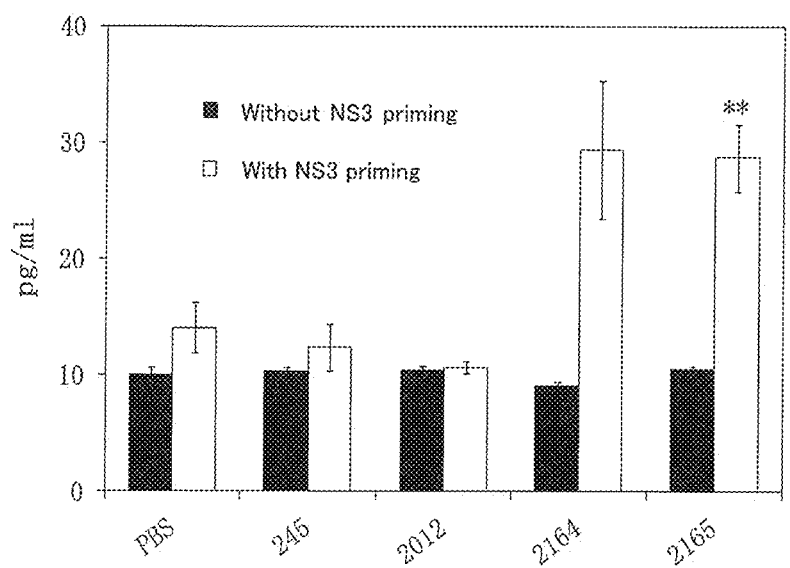
FIG. 7 is a graph showing a comparison of IFN-γ amounts in mouse spleenocytes with and without NS3 antigen priming in various administration groups including the *Bifidobacterium longum* 2164 administration group and the *Bifidobacterium longum* 2165 administration group.

The result is shown in FIG. 7. The vertical axis of FIG. 7 indicates the amount of IFN-γ (pg/ml) in supernatant of the cultured spleenocytes. From the left, *Bifidobacterium longum* 245 administration group, *Bifidobacterium longum* 2012 administration group, *Bifidobacterium longum* 2164 administration group, and *Bifidobacterium longum* 2165 administration group are shown, and a black column graph expresses "without NS3 antigen priming" (control group) and a white column graph expresses "with NS3 antigen priming". In the *Bifidobacterium longum* 2165 administration group, the IFN-γ production amount increased with priming, and a significant difference ($p<0.01$) was observed compared to a non-priming control group cultured under the same conditions. In the *Bifidobacterium longum* 2164 administration group, no significant difference was observed, but the IFN-γ production amount was increased with priming.

Example 5: Design 2 of HCV NS3 Polypeptide Gene for *Bifidobacterium* Cell Surface Expression An amino acid sequence shown in FIG. 8 was designed such that the NS3-derived antigenic peptides were linked to the N-terminus and C-terminus of the base domain that was based on the NS3 α-helical domain (position 1510 to position 1657) of the HCV type 1b polypeptide.

In the amino acid sequence of FIG. 8 (SEQ. ID. No. 32), a region including QSFLATCINGVCWTVYHGAG (position 1067 to position 1086, CD8 Epitope 1: SEQ. ID. No. 4) is linked on the N-terminal side of the base domain, and a region including EIPFYGKAI (position 1372 to position 1380, CD8 Epitope 4: SEQ. ID. No. 7), KLSALGVNA (position 1406 to position 1414, CD8 Epitope 6: SEQ. ID. No. 9), and VATDALMTGYTGDFDSVIDC (position 1435 to position 1454, CD8 Epitope 7: SEQ. ID. No. 10) in this order is linked on the C-terminal side of the base domain. The base domain is a region corresponding to position 1510 to position 1657 of the HCV type 1b antigenic polypeptide, and includes TPAETSVRLRAYLNTPG (position 1531 to position 1547, CD4 Epitope 4: SEQ. ID. No. 15) and GAVQNEVTL (position 1629 to position 1637, CD8 Epitope 8: SEQ. ID. No. 11).

A gene sequence (SEQ. ID. No. 33; the corresponding amino acid sequence is indicated by SEQ. ID. No. 34) was designed based on the amino acid sequence of FIG. 8, in accordance with the codon usage frequency of a bifidobacteria (http://www.kazusa.or.jp/codon/).

Example 6: Design 3 of HCV NS3 Polypeptide Gene for *Bifidobacterium* Cell Surface Expression An amino acid sequence shown in FIG. 9 was designed such that the NS3-derived antigenic peptides were linked to the N-terminus and C-terminus of the base domain that was based on the NS3 downstream β-α-β-domain (position 1351 to position 1509) of the HCV type 1b polypeptide. In the base domain, three amino acids from position 1351 to position 1353 were deleted, two Ks (lysines) at positions 1398 and 1399 were substituted by Q (glutamine: position 1398) and L (leucine: position 1399).

In the amino acid sequence of FIG. 9 (SEQ. ID. No. 35), a region including QSFLATCINGVCWTVYHGAG (position 1067 to position 1086, CD8 Epitope 1: SEQ. ID. No. 4) is linked on the N-terminal side of the base domain, and a region including TPAETSVRLRAYLNTPG (position 1531 to position 1547, CD4 Epitope 4: SEQ. ID. No. 15) is linked on the C-terminal side of the base domain. The base domain itself includes EIPFYGKAI (position 1372 to position 1380, CD8 Epitope 4: SEQ. ID. No. 7), LIFCHSKQL (position 1391 to position 1399, KK of CD8 Epitope 5 are substituted with QL: SEQ. ID. No. 21), KLSALGVNA (position 1406 to position 1414, CD8 Epitope 6: SEQ. ID. No. 9), and VATDALMTGYTGDFDSVIDC (position 1435 to position 1454, CD8 Epitope 7: SEQ. ID. No. 10).

A gene sequence (SEQ. ID. No. 36; the corresponding amino acid sequence is indicated by SEQ. ID. No. 37) was designed based on the amino acid sequence of FIG. 9, in accordance with the codon usage frequency of a bifidobacteria (http://www.kazusa.or.jp/codon/).

Example 7: Design 4 of HCV NS3 Polypeptide Gene for *Bifidobacterium* Cell Surface Expression An amino acid sequence shown in FIG. 10 was designed such that the NS3-derived antigenic peptide was linked to the C-terminus of the base domain that was based on the NS3 β-barrel domain (position 1027 to position 1195) in which a part (position 1677 to position 1690) of the NS4A region of HCV type 1b polypeptide was linked to its N-terminus. In the base domain, two amino acids at positions 1027 and 1028 and an amino acid at position 1195 were deleted, and two Rs (arginines) at positions 1144 and 1145 were substituted with Q (glutamine: position 1144) and L (leucine: position 1145).

In the amino acid sequence of FIG. 10 (SEQ. ID. No. 38), the region of Base Domain (1) including ETTMRSPVFTDNSTPPAVP (position 1202 to position 1220, CD4 Epitope 2: SEQ. ID. No. 13), ITYSTYGK (position 1291 to position 1298, CD8 Epitope 3: SEQ. ID. No. 6), and GGCSGGAYDIIICDECHSTDSTSILGIG (position 1303 to position 1330, CD4 Epitope 3: SEQ. ID. No. 14), and a region including EIPFYGKAI (position 1372 to position 1380, CD8 Epitope 4: SEQ. ID. No. 7), KLSALGVNA (position 1406 to position 1414, CD8 Epitope 6: SEQ. ID. No. 9), and VATDALMTGYTGDFDSVIDC (position 1435 to position 1454, CD8 Epitope 7: SEQ. ID. No. 10) in this order are linked on the C-terminal side of the base domain. The base domain itself that is based on the NS4A region and NS3 β-barrel domain includes QSFLATCINGVCWTVYHGAG (position 1067 to position 1086, CD8 Epitope 1: SEQ. ID. No. 4), LYLVTRHADVIPVRQLGDSR (position 1130 to position 1149, RR of CD4 Epitope 1 are substituted with QL: SEQ. ID. No. 22), and LLCPSGHVV (position 1169 to position 1177, CD8 Epitope 2: SEQ. ID. No. 5).

A gene sequence (SEQ. ID. No. 39; the corresponding amino acid sequence is indicated by SEQ. ID. No. 40) was designed based on the amino acid sequence of FIG. 10, in accordance with the codon usage frequency of a *bifidobacterium* (http://www.kazusa.or.jp/codon/).

Example 8: Production of Transformed EL 4 Cells for Subcutaneous Tumor

Because the mouse is not infected with HCV, a subcutaneous tumor was generated in the mouse and the following experiment was performed in order to evaluate the effects of the vaccine of the present invention based on the effects of inhibiting tumor growth.

A fragment encoding NS3/4A was cut out from a plasmid pSG5/NS3/4A using BamHI and the fragment was inserted into a BamHI site of a plasmid pBApo-CMV Neo (TAKARA BIO Inc.), and thereby a plasmid pBApo-CMV Neo/NS3/4A was obtained (FIG. 11). The plasmid pBApo-CMV Neo/NS3/4A was prepared and introduced into an EL4 cell (mouse lymphoma cell) using TransIT-293 Transfection Reagent (TAKARA BIO Inc.). Transformed EL4 cells were selected in a culture medium containing 800 μg/ml of G418, and clonal strains of the transformed EL4 cells (NS3/4A-EL4 cells) were obtained by limiting dilution.

In order to confirm that the obtained cells were the transformed cells, RT-PCR and Western blotting were performed. RT-PCR was conventionally performed, specifically, cDNA was prepared from total RNA, and a DNA fragment encoding NS3/4A was amplified by the incubation of 94° C. for 120 seconds, followed by 30 cycles of 98° C. for 10 seconds, 64° C. for 30 seconds, and 68° C. for 40 seconds, with primers (SEQ. ID. No. 41: CGGCCCTCAGGCATGTTCGATTCTTC, SEQ. ID. No. 42: CCGGACAAGATGATCCTGCCCACAATG), was subjected to agarose gel electrophoresis, and was then stained with ethidium bromide to observe the amplified DNA fragments under UV (FIG. 12). In FIG. 12, lane 1 for the plasmid pSG5/NS3/4A, lane 2 for transformed EL4 cells, and lane 3 for Mock infected EL4 cells, intended bands were observed in lanes 1 and 2.

Figure 13:
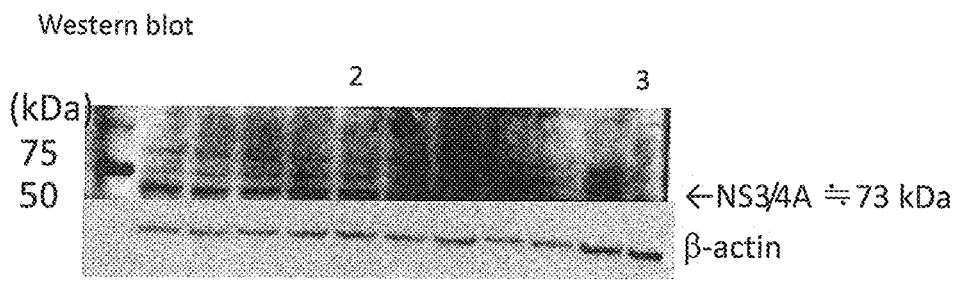
FIG. 13 shows the detection of NS3/4A by Western blotting.

Western blotting was performed by fractionating cell extract by SDS-PAGE, transferring proteins to a nylon membrane, performing blocking, and then detecting NS3/4A protein using antibodies (FIG. 13). In FIG. 13, the band of 73 kDa NS3/4A protein was detected in the transformed EL4 cells (lane 2). Also, the band of the NS3/4A protein was not detected in lane 3 for a control. Accordingly, it was confirmed that the obtained cells were the clonal strains of the NS3/4A-EL4 cells.

Example 9: Examination on Anti-Tumor Effects of Oral Administration of *B. longum* 2165

On the day before subcutaneous inoculation (Day 0), the C57BL/6N mice was weighed, and transplanted subcutaneously with the NS3/4A-EL4 cells, which were confirmed to be transformants. For the transplantation, 1×10⁶ cells embedded into 200 μl of RPMI1640 & Matrigel were inoculated subcutaneously. When the day of subcutaneous inoculation was Day 1, experiment for oral administration of bifidobacteria expressing a NS3/4A protein on its cell surface was started.

Figure 14:
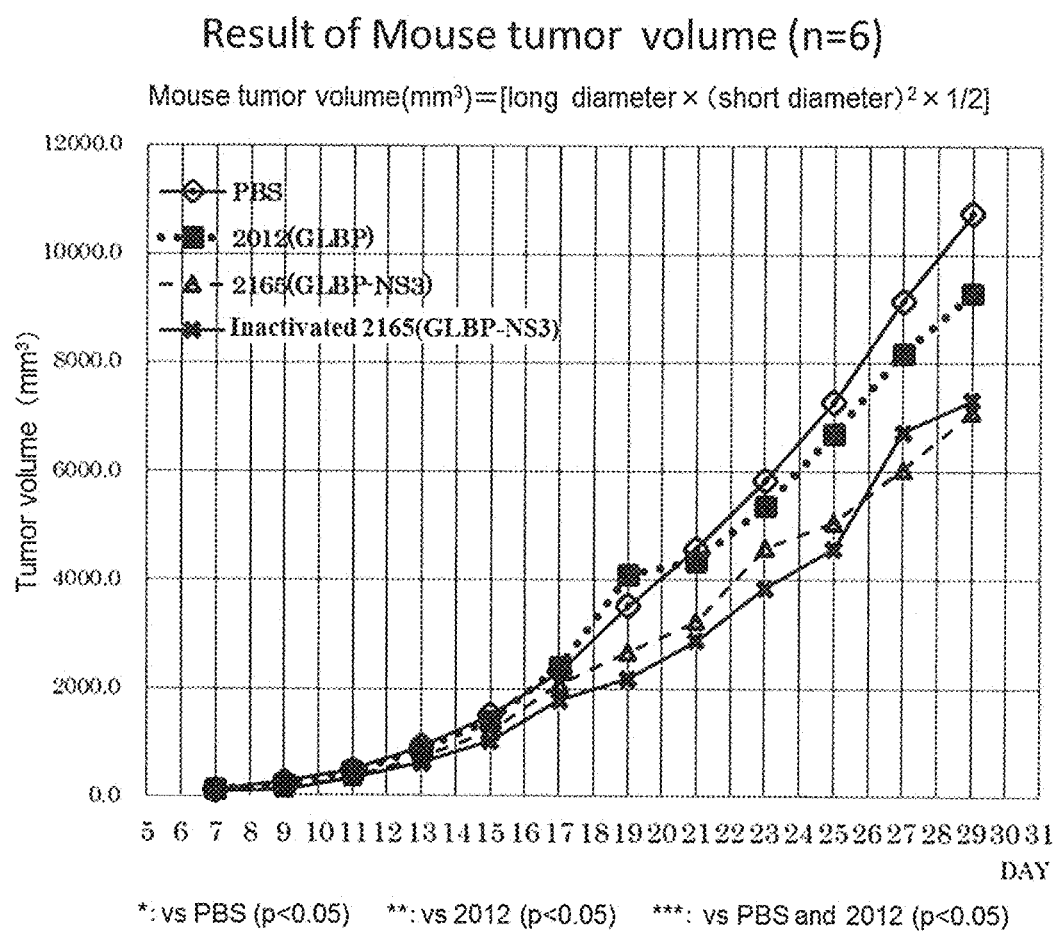
FIG. 14 shows the effects of a NS3-expressing *bifidobacterium* vaccine relating to the inhibition of the growth of EL4 cells expressing NS3/4A.

For the oral administration group, PBS, *B. longum* 2012 (GLBP gene expression strain), *B. longum* 2165 (GLBP-NS3 gene expression strain), and inactivated *B. longum* 2165 (5×10⁸ CFU/ml, 250 μl of bacterial culture was heated at 65° C. for 5 minutes) were administered to the experiment sections of six mice for each experiment section, respectively, three times per week with a solution of 5×10⁷ CFU in 100 μl of PBS (13 times in total). Thereafter, a long diameter and a short diameter of a tumor were measured every two days. The result thereof is shown in FIG. 14. As shown in FIG. 14, tumor volume markedly increased in the PBS and GLBP administration sections, but an increase in tumor volume was significantly inhibited in 2165 (GLBP-NS3) and inactivated 2165(GLBP-NS3) administration sections. This indicated that GLBP-NS3 gene expression bifidobacteria had effects on the inhibition of proliferation of tumor cells expressing a NS3/4A protein on the cell surface. Also, these effects were observed not only in viable bacteria but also in inactivated bacteria. Therefore, it is considered that the protein has effects as an antigen regardless of whether the bifidobacteria are dead or alive.

INDUSTRIAL APPLICABILITY

According to the present invention, a polypeptide having immunogenicity can be expressed and presented on the cell surface of bifidobacteria. Furthermore, according to the present invention, an NS3-specific immunity can be induced in an animal orally administered with bifidobacteria presenting a hepatitis C virus antigenic polypeptide on the cell surface of the bifidobacteria, for example, which can be utilized as a vaccine composition (oral vaccine, for example). Such a vaccine composition is expected to increase a cure rate of HCV chronic infection in combination with an existing interferon therapy or the like.

The invention claimed is:

1. A polynucleic acid for expressing an immunogenic polypeptide on a cell surface of a *bifidobacterium*, comprising:
   a gene encoding the immunogenic polypeptide,
   wherein the immunogenic polypeptide is a hepatitis C virus antigenic polypeptide and wherein the immunogenic polypeptide comprises the amino acid sequence of SEQ ID NO: 23.

2. The polynucleic acid for expressing an immunogenic polypeptide on a cell surface of a *bifidobacterium* according to claim 1, further comprising a gene encoding a *bifidobacterium*-derived galacto-N-biose/lacto-N-biose (GNB/LNB) substrate-binding membrane protein, wherein the gene encoding the immunogenic polypeptide is positioned 3' to the gene encoding the *bifidobacterium*-derived GNB/LNB substrate-binding membrane protein.

3. A vector for gene expression, comprising the polynucleic acid for expressing an immunogenic polypeptide on a cell surface of a *bifidobacterium* according to claim 2 in an expressible form.

4. A transformed *bifidobacterium*, harboring the vector according to claim 3 to present the immunogenic polypeptide on a cell surface.

5. A transformed *bifidobacterium*, comprising, in a genome, the polynucleic acid for expressing an immunogenic polypeptide on a cell surface of a *bifidobacterium* according to claim 2 in an expressible form to present the immunogenic polypeptide on a cell surface.

6. A vaccine composition for hepatitis C, comprising the transformed *bifidobacterium* according to claim 4.

7. The vaccine composition according to claim 6, which is an oral vaccine.

8. A vaccine composition for hepatitis C, comprising the transformed *bifidobacterium* according to claim 5.

9. A polynucleic acid for expressing an immunogenic polypeptide on a cell surface of a *bifidobacterium*, comprising:
   a gene encoding the immunogenic polypeptide,
   wherein the immunogenic polypeptide is a hepatitis C virus antigenic polypeptide and wherein the immunogenic polypeptide comprises the amino acid sequence of SEQ ID NO: 24.

10. The polynucleic acid for expressing an immunogenic polypeptide on a cell surface of a *bifidobacterium* according to claim 9, further comprising a gene encoding a *bifidobacterium*-derived galacto-N-biose/lacto-N-biose (GNB/LNB) substrate-binding membrane protein, wherein the gene encoding the immunogenic polypeptide is positioned 3' to the gene encoding the *bifidobacterium*-derived GNB/LNB substrate-binding membrane protein.

11. A vector for gene expression, comprising the polynucleic acid for expressing an immunogenic polypeptide on a cell surface of a *bifidobacterium* according to claim 10 in an expressible form.

12. A transformed *bifidobacterium*, harboring the vector according to claim 11 to present the immunogenic polypeptide on a cell surface.

13. A transformed *bifidobacterium*, comprising, in a genome, the polynucleic acid for expressing an immunogenic polypeptide on a cell surface of a *bifidobacterium* according to claim 10 in an expressible form to present the immunogenic polypeptide on a cell surface.

14. A vaccine composition for hepatitis C, comprising the transformed *bifidobacterium* according to claim 12.

15. The vaccine composition according to claim 14, which is an oral vaccine.

16. A vaccine composition for hepatitis C, comprising the transformed *bifidobacterium* according to claim 13.

* * * * *

```
                           SEQUENCE LISTING

<160> NUMBER OF SEQ ID NOS: 42

<210> SEQ ID NO 1
<211> LENGTH: 1317
<212> TYPE: DNA
<213> ORGANISM: Bifidobacterium longum subsp. longum JCM1217
<220> FEATURE:
<221> NAME/KEY: CDS
<222> LOCATION: (1)..(1317)
<223> OTHER INFORMATION: GLBP

<400> SEQUENCE: 1 atg gta tct cgc aat aag cgc atc gtg gct gct ttt gcc gcg gta gca       48
Met Val Ser Arg Asn Lys Arg Ile Val Ala Ala Phe Ala Ala Val Ala
1               5                  10                  15 gca atg gga atg ggc ttg gcc ggt tgc ggc agc gac act gcc ggc gac       96
Ala Met Gly Met Gly Leu Ala Gly Cys Gly Ser Asp Thr Ala Gly Asp
            20                  25                  30 acg aag acc acc gat gat ggt ggc gtg gtc aac atc acc tac atg cac      144
Thr Lys Thr Thr Asp Asp Gly Gly Val Val Asn Ile Thr Tyr Met His
        35                  40                  45 cgt ctg ccg gat tcc gag ggc atg act ctg gtc aac gac atc gtt gcc      192
Arg Leu Pro Asp Ser Glu Gly Met Thr Leu Val Asn Asp Ile Val Ala
    50                  55                  60 aag tgg aat aag cag cat ccg gat att cag gtc aag gcc acc aag ttc      240
Lys Trp Asn Lys Gln His Pro Asp Ile Gln Val Lys Ala Thr Lys Phe
65                  70                  75                  80 gat ggt aag gcc tct gac atg atc aag aag ctt gag acc gac gtc aag      288
Asp Gly Lys Ala Ser Asp Met Ile Lys Lys Leu Glu Thr Asp Val Lys
                85                  90                  95 tcc ggc gag gct ccg gat ctg gct cag gtc ggt tac gcc gag ctg cct      336
Ser Gly Glu Ala Pro Asp Leu Ala Gln Val Gly Tyr Ala Glu Leu Pro
            100                 105                 110 gag gtc ttc acc aag ggt ctg ctg cag gat gtg acc cag tat gcc gag      384
Glu Val Phe Thr Lys Gly Leu Leu Gln Asp Val Thr Gln Tyr Ala Glu
        115                 120                 125 cag tac aag aac gac ttc gca tcc ggc ccg tac agc ctg gtt cag gtt      432
Gln Tyr Lys Asn Asp Phe Ala Ser Gly Pro Tyr Ser Leu Val Gln Val
    130                 135                 140 ggc ggc aag gct tac ggc ctg ccg cag gac acc ggc ccg ctg gtt tac      480
Gly Gly Lys Ala Tyr Gly Leu Pro Gln Asp Thr Gly Pro Leu Val Tyr
145                 150                 155                 160 ttc tac aac aag gct gag ttc gag aag ctc ggc atc acc gag att ccg      528
Phe Tyr Asn Lys Ala Glu Phe Glu Lys Leu Gly Ile Thr Glu Ile Pro
                165                 170                 175 cag acc gcc gat gag ttt atc gcc gct gcc aag acc gct gcc gcc gct      576
Gln Thr Ala Asp Glu Phe Ile Ala Ala Ala Lys Thr Ala Ala Ala Ala
            180                 185                 190 ggc aag tac atc atg tcc tac cag cct gat gag gcc ggc aac atg atc      624
Gly Lys Tyr Ile Met Ser Tyr Gln Pro Asp Glu Ala Gly Asn Met Ile
        195                 200                 205 tcc ggt ctg gct ggc gcc tcc ggt ggt tgg tac aag gtg aag ggc gac      672
Ser Gly Leu Ala Gly Ala Ser Gly Gly Trp Tyr Lys Val Lys Gly Asp
    210                 215                 220 tcc tgg gtc gtc aac acc gag acc gat ggc tcc aag gca acc gct gac      720
Ser Trp Val Val Asn Thr Glu Thr Asp Gly Ser Lys Ala Thr Ala Asp
225                 230                 235                 240
```

| | | |
|---|---|---|
| ttc tac cag cag ctg ctc gac gcc aag gca gcc acc acc aac ccg cgt<br>Phe Tyr Gln Gln Leu Leu Asp Ala Lys Ala Ala Thr Thr Asn Pro Arg<br>245 250 255 | | 768 |
| tgg gat ccg tcc ttc gat gca tcc atc aag gat ggc tcg ttg atc ggt<br>Trp Asp Pro Ser Phe Asp Ala Ser Ile Lys Asp Gly Ser Leu Ile Gly<br>260 265 270 | | 816 |
| act gtg gcc gcc gct tgg gaa gcc ccg ctg ttc atg acc tcc tcc ggt<br>Thr Val Ala Ala Ala Trp Glu Ala Pro Leu Phe Met Thr Ser Ser Gly<br>275 280 285 | | 864 |
| ggc acc ggc tcc ggc gaa tgg cag gtc gct cag ctc ggt gac tgg ttc<br>Gly Thr Gly Ser Gly Glu Trp Gln Val Ala Gln Leu Gly Asp Trp Phe<br>290 295 300 | | 912 |
| ggc aac gct ggc aag acc ggc cct gac ggt ggt tcc gcc gtg gcc gtg<br>Gly Asn Ala Gly Lys Thr Gly Pro Asp Gly Gly Ser Ala Val Ala Val<br>305 310 315 320 | | 960 |
| ctg aag aac tcc aag cac ccg aag gaa gca atg gag ttc ctg gat tgg<br>Leu Lys Asn Ser Lys His Pro Lys Glu Ala Met Glu Phe Leu Asp Trp<br>325 330 335 | | 1008 |
| ttc aac acc cag gtt cct gat ctg gtt tcc cag ggc ctc gtg ccg gct<br>Phe Asn Thr Gln Val Pro Asp Leu Val Ser Gln Gly Leu Val Pro Ala<br>340 345 350 | | 1056 |
| gct acc act gaa gac gct gag act cct tcc gag tgg tcc acc ttc ttc<br>Ala Thr Thr Glu Asp Ala Glu Thr Pro Ser Glu Trp Ser Thr Phe Phe<br>355 360 365 | | 1104 |
| ggt ggt cag gac atc atg aag gaa ttc aag acc gct aac aac aac atg<br>Gly Gly Gln Asp Ile Met Lys Glu Phe Lys Thr Ala Asn Asn Asn Met<br>370 375 380 | | 1152 |
| ggt gac ttc acc tac atg cct ggc ttc tcc gca gtc gcc gcc aag atg<br>Gly Asp Phe Thr Tyr Met Pro Gly Phe Ser Ala Val Ala Ala Lys Met<br>385 390 395 400 | | 1200 |
| aac gaa acc gcc gcc aag gcc acc gat ggc tcc ggc aag gtt gca gac<br>Asn Glu Thr Ala Ala Lys Ala Thr Asp Gly Ser Gly Lys Val Ala Asp<br>405 410 415 | | 1248 |
| atc ttc tcc gac gca cag acc acc tct gtg gat acg ctg aag aac ttc<br>Ile Phe Ser Asp Ala Gln Thr Thr Ser Val Asp Thr Leu Lys Asn Phe<br>420 425 430 | | 1296 |
| ggc ctg tct gtt tcc gag tga<br>Gly Leu Ser Val Ser Glu<br>435 | | 1317 |

<210> SEQ ID NO 2
<211> LENGTH: 438
<212> TYPE: PRT
<213> ORGANISM: Bifidobacterium longum subsp. longum JCM1217

<400> SEQUENCE: 2

Met Val Ser Arg Asn Lys Arg Ile Val Ala Ala Phe Ala Ala Val Ala
1               5                   10                  15

Ala Met Gly Met Gly Leu Ala Gly Cys Gly Ser Asp Thr Ala Gly Asp
            20                  25                  30

Thr Lys Thr Thr Asp Asp Gly Gly Val Val Asn Ile Thr Tyr Met His
        35                  40                  45

Arg Leu Pro Asp Ser Glu Gly Met Thr Leu Val Asn Asp Ile Val Ala
    50                  55                  60

Lys Trp Asn Lys Gln His Pro Asp Ile Gln Val Lys Ala Thr Lys Phe
65                  70                  75                  80

Asp Gly Lys Ala Ser Asp Met Ile Lys Lys Leu Glu Thr Asp Val Lys
                85                  90                  95

```
Ser Gly Glu Ala Pro Asp Leu Ala Gln Val Gly Tyr Ala Glu Leu Pro
            100                 105                 110

Glu Val Phe Thr Lys Gly Leu Leu Gln Asp Val Thr Gln Tyr Ala Glu
        115                 120                 125

Gln Tyr Lys Asn Asp Phe Ala Ser Gly Pro Tyr Ser Leu Val Gln Val
    130                 135                 140

Gly Gly Lys Ala Tyr Gly Leu Pro Gln Asp Thr Gly Pro Leu Val Tyr
145                 150                 155                 160

Phe Tyr Asn Lys Ala Glu Phe Glu Lys Leu Gly Ile Thr Glu Ile Pro
                165                 170                 175

Gln Thr Ala Asp Glu Phe Ile Ala Ala Ala Lys Thr Ala Ala Ala Ala
            180                 185                 190

Gly Lys Tyr Ile Met Ser Tyr Gln Pro Asp Glu Ala Gly Asn Met Ile
        195                 200                 205

Ser Gly Leu Ala Gly Ala Ser Gly Gly Trp Tyr Lys Val Lys Gly Asp
    210                 215                 220

Ser Trp Val Val Asn Thr Glu Thr Asp Gly Ser Lys Ala Thr Ala Asp
225                 230                 235                 240

Phe Tyr Gln Gln Leu Leu Asp Ala Lys Ala Ala Thr Thr Asn Pro Arg
                245                 250                 255

Trp Asp Pro Ser Phe Asp Ala Ser Ile Lys Asp Gly Ser Leu Ile Gly
            260                 265                 270

Thr Val Ala Ala Ala Trp Glu Ala Pro Leu Phe Met Thr Ser Ser Gly
        275                 280                 285

Gly Thr Gly Ser Gly Glu Trp Gln Val Ala Gln Leu Gly Asp Trp Phe
    290                 295                 300

Gly Asn Ala Gly Lys Thr Gly Pro Asp Gly Gly Ser Ala Val Ala Val
305                 310                 315                 320

Leu Lys Asn Ser Lys His Pro Lys Glu Ala Met Glu Phe Leu Asp Trp
                325                 330                 335

Phe Asn Thr Gln Val Pro Asp Leu Val Ser Gln Gly Leu Val Pro Ala
            340                 345                 350

Ala Thr Thr Glu Asp Ala Glu Thr Pro Ser Glu Trp Ser Thr Phe Phe
        355                 360                 365

Gly Gly Gln Asp Ile Met Lys Glu Phe Lys Thr Ala Asn Asn Asn Met
    370                 375                 380

Gly Asp Phe Thr Tyr Met Pro Gly Phe Ser Ala Val Ala Ala Lys Met
385                 390                 395                 400

Asn Glu Thr Ala Ala Lys Ala Thr Asp Gly Ser Gly Lys Val Ala Asp
                405                 410                 415

Ile Phe Ser Asp Ala Gln Thr Thr Ser Val Asp Thr Leu Lys Asn Phe
            420                 425                 430

Gly Leu Ser Val Ser Glu
        435

<210> SEQ ID NO 3
<211> LENGTH: 660
<212> TYPE: PRT
<213> ORGANISM: Hepatitis C virus

<400> SEQUENCE: 3

Gln Gly Trp Arg Leu Leu Ala Pro Ile Thr Ala Tyr Ser Gln Gln Thr
1               5                   10                  15

Arg Gly Leu Leu Gly Cys Ile Ile Thr Ser Leu Thr Gly Arg Asp Lys
            20                  25                  30
```

-continued

```
Asn Gln Val Glu Gly Glu Val Gln Val Ser Thr Ala Thr Gln Ser
            35                  40                  45
Phe Leu Ala Thr Cys Ile Asn Gly Val Cys Trp Thr Val Tyr His Gly
 50                  55                  60
Ala Gly Ser Lys Thr Leu Ala Gly Pro Lys Gly Pro Ile Thr Gln Met
 65                  70                  75                  80
Tyr Thr Asn Val Asp Gln Asp Leu Val Gly Trp Pro Ala Pro Pro Gly
                 85                  90                  95
Ala Arg Ser Met Thr Pro Cys Thr Cys Gly Ser Ser Asp Leu Tyr Leu
                100                 105                 110
Val Thr Arg His Ala Asp Val Ile Pro Val Arg Arg Arg Gly Asp Ser
             115                 120                 125
Arg Gly Ser Leu Leu Ser Pro Arg Pro Ile Ser Tyr Leu Lys Gly Ser
 130                 135                 140
Ser Gly Gly Pro Leu Leu Cys Pro Ser Gly His Val Val Gly Ile Phe
 145                 150                 155                 160
Arg Ala Ala Val Cys Thr Arg Gly Val Ala Lys Ala Val Asp Phe Val
                 165                 170                 175
Pro Val Glu Ser Met Glu Thr Thr Met Arg Ser Pro Val Phe Thr Asp
             180                 185                 190
Asn Ser Thr Pro Pro Ala Val Pro Gln Ser Phe Gln Val Ala His Leu
 195                 200                 205
His Ala Pro Thr Gly Ser Gly Lys Ser Thr Lys Val Pro Ala Ala Tyr
 210                 215                 220
Ala Ala Gln Gly Tyr Lys Val Leu Val Leu Asn Pro Ser Val Ala Ala
 225                 230                 235                 240
Thr Leu Gly Phe Gly Ala Tyr Met Ser Lys Ala His Gly Val Asp Pro
                 245                 250                 255
Asn Ile Arg Thr Gly Val Arg Thr Ile Thr Thr Gly Ala Pro Ile Thr
             260                 265                 270
Tyr Ser Thr Tyr Gly Lys Phe Leu Ala Asp Gly Gly Cys Ser Gly Gly
         275                 280                 285
Ala Tyr Asp Ile Ile Ile Cys Asp Glu Cys His Ser Thr Asp Ser Thr
 290                 295                 300
Ser Ile Leu Gly Ile Gly Thr Val Leu Asp Gln Ala Glu Thr Ala Gly
 305                 310                 315                 320
Ala Arg Leu Val Val Leu Ala Thr Ala Thr Pro Pro Gly Ser Val Thr
                 325                 330                 335
Val Pro His Pro Asn Ile Glu Glu Val Ala Leu Ser Asn Thr Gly Glu
             340                 345                 350
Ile Pro Phe Tyr Gly Lys Ala Ile Pro Leu Glu Ala Ile Lys Gly Gly
         355                 360                 365
Arg His Leu Ile Phe Cys His Ser Lys Lys Lys Cys Asp Glu Leu Ala
 370                 375                 380
Ala Lys Leu Ser Ala Leu Gly Val Asn Ala Val Ala Tyr Tyr Arg Gly
 385                 390                 395                 400
Leu Asp Val Ser Ile Ile Pro Thr Ser Gly Asp Val Val Val Val Ala
                 405                 410                 415
Thr Asp Ala Leu Met Thr Gly Tyr Thr Gly Asp Phe Asp Ser Val Ile
             420                 425                 430
Asp Cys Asn Thr Cys Val Thr Gln Thr Val Asp Phe Ser Leu Asp Pro
 435                 440                 445
```

```
Thr Phe Thr Ile Glu Thr Thr Thr Val Pro Gln Asp Ala Val Ser Arg
        450                 455                 460
Ser Gln Arg Arg Gly Arg Thr Gly Arg Gly Gly Ile Tyr Arg
465                 470                 475                 480
Phe Val Thr Pro Gly Glu Arg Pro Ser Gly Met Phe Asp Ser Ser Val
                    485                 490                 495
Leu Cys Glu Cys Tyr Asp Ala Gly Cys Ala Trp Tyr Glu Leu Thr Pro
                500                 505                 510
Ala Glu Thr Ser Val Arg Leu Arg Ala Tyr Leu Asn Thr Pro Gly Leu
            515                 520                 525
Pro Val Cys Gln Asp His Leu Glu Phe Trp Glu Ser Val Phe Thr Gly
        530                 535                 540
Leu Thr His Ile Asp Ala His Phe Leu Ser Gln Thr Lys Gln Ala Gly
545                 550                 555                 560
Asp Asn Phe Pro Tyr Leu Val Ala Tyr Gln Ala Thr Val Cys Ala Arg
                    565                 570                 575
Ala Lys Ala Pro Pro Ser Trp Asp Gln Met Trp Lys Cys Leu Ile
                580                 585                 590
Arg Leu Lys Pro Thr Leu His Gly Pro Thr Pro Leu Leu Tyr Arg Leu
            595                 600                 605
Gly Ala Val Gln Asn Glu Val Thr Leu Thr His Pro Ile Thr Lys Phe
        610                 615                 620
Ile Met Ala Cys Met Ser Ala Asp Leu Glu Val Val Thr Ser Thr Trp
625                 630                 635                 640
Val Leu Val Gly Gly Val Leu Ala Ala Leu Ala Ala Tyr Cys Leu Thr
                    645                 650                 655
Thr Gly Ser Val
            660

<210> SEQ ID NO 4
<211> LENGTH: 20
<212> TYPE: PRT
<213> ORGANISM: Hepatitis C virus

<400> SEQUENCE: 4

Gln Ser Phe Leu Ala Thr Cys Ile Asn Gly Val Cys Trp Thr Val Tyr
1               5                   10                  15

His Gly Ala Gly
            20

<210> SEQ ID NO 5
<211> LENGTH: 9
<212> TYPE: PRT
<213> ORGANISM: Hepatitis C virus

<400> SEQUENCE: 5

Leu Leu Cys Pro Ser Gly His Val Val
1               5

<210> SEQ ID NO 6
<211> LENGTH: 8
<212> TYPE: PRT
<213> ORGANISM: Hepatitis C virus

<400> SEQUENCE: 6

Ile Thr Tyr Ser Thr Tyr Gly Lys
1               5
```

-continued

```
<210> SEQ ID NO 7
<211> LENGTH: 9
<212> TYPE: PRT
<213> ORGANISM: Hepatitis C virus

<400> SEQUENCE: 7

Glu Ile Pro Phe Tyr Gly Lys Ala Ile
1               5

<210> SEQ ID NO 8
<211> LENGTH: 9
<212> TYPE: PRT
<213> ORGANISM: Hepatitis C virus

<400> SEQUENCE: 8

Leu Ile Phe Cys His Ser Lys Lys Lys
1               5

<210> SEQ ID NO 9
<211> LENGTH: 9
<212> TYPE: PRT
<213> ORGANISM: Hepatitis C virus

<400> SEQUENCE: 9

Lys Leu Ser Ala Leu Gly Val Asn Ala
1               5

<210> SEQ ID NO 10
<211> LENGTH: 20
<212> TYPE: PRT
<213> ORGANISM: Hepatitis C virus

<400> SEQUENCE: 10

Val Ala Thr Asp Ala Leu Met Thr Gly Tyr Thr Gly Asp Phe Asp Ser
1               5                   10                  15

Val Ile Asp Cys
            20

<210> SEQ ID NO 11
<211> LENGTH: 9
<212> TYPE: PRT
<213> ORGANISM: Hepatitis C virus

<400> SEQUENCE: 11

Gly Ala Val Gln Asn Glu Val Thr Leu
1               5

<210> SEQ ID NO 12
<211> LENGTH: 20
<212> TYPE: PRT
<213> ORGANISM: Hepatitis C virus

<400> SEQUENCE: 12

Leu Tyr Leu Val Thr Arg His Ala Asp Val Ile Pro Val Arg Arg Arg
1               5                   10                  15

Gly Asp Ser Arg
            20

<210> SEQ ID NO 13
<211> LENGTH: 19
<212> TYPE: PRT
<213> ORGANISM: Hepatitis C virus
```

```
<400> SEQUENCE: 13

Glu Thr Thr Met Arg Ser Pro Val Phe Thr Asp Asn Ser Thr Pro Pro
1               5                   10                  15

Ala Val Pro

<210> SEQ ID NO 14
<211> LENGTH: 28
<212> TYPE: PRT
<213> ORGANISM: Hepatitis C virus

<400> SEQUENCE: 14

Gly Gly Cys Ser Gly Gly Ala Tyr Asp Ile Ile Ile Cys Asp Glu Cys
1               5                   10                  15

His Ser Thr Asp Ser Thr Ser Ile Leu Gly Ile Gly
            20                  25

<210> SEQ ID NO 15
<211> LENGTH: 17
<212> TYPE: PRT
<213> ORGANISM: Hepatitis C virus

<400> SEQUENCE: 15

Thr Pro Ala Glu Thr Ser Val Arg Leu Arg Ala Tyr Leu Asn Thr Pro
1               5                   10                  15

Gly

<210> SEQ ID NO 16
<211> LENGTH: 155
<212> TYPE: PRT
<213> ORGANISM: Artificial
<220> FEATURE:
<223> OTHER INFORMATION: NS3 based platform domain 1

<400> SEQUENCE: 16

Val Pro Val Glu Ser Met Glu Thr Thr Met Arg Ser Pro Val Phe Thr
1               5                   10                  15

Asp Asn Ser Thr Pro Pro Ala Val Pro Gln Ser Phe Gln Val Ala His
            20                  25                  30

Leu His Ala Pro Thr Gly Ser Gly Lys Ser Thr Lys Val Pro Ala Ala
        35                  40                  45

Tyr Ala Ala Gln Gly Tyr Lys Val Leu Val Leu Asn Pro Ser Val Ala
    50                  55                  60

Ala Thr Leu Gly Phe Gly Ala Tyr Met Ser Lys Ala His Gly Val Asp
65                  70                  75                  80

Pro Asn Ile Arg Thr Gly Val Arg Thr Ile Thr Thr Gly Ala Pro Ile
                85                  90                  95

Thr Tyr Ser Thr Tyr Gly Lys Phe Leu Ala Asp Gly Gly Cys Ser Gly
            100                 105                 110

Gly Ala Tyr Asp Ile Ile Ile Cys Asp Glu Cys His Ser Thr Asp Ser
        115                 120                 125

Thr Ser Ile Leu Gly Ile Gly Thr Val Leu Asp Gln Ala Glu Thr Ala
    130                 135                 140

Gly Ala Arg Leu Val Val Leu Ala Thr Ala Thr
145                 150                 155

<210> SEQ ID NO 17
<211> LENGTH: 148
<212> TYPE: PRT
<213> ORGANISM: Artificial
```

<220> FEATURE:
<223> OTHER INFORMATION: NS3 based platform domain 2

<400> SEQUENCE: 17

```
Gly Met Phe Asp Ser Ser Val Leu Cys Glu Cys Tyr Asp Ala Gly Cys
1               5                   10                  15

Ala Trp Tyr Glu Leu Thr Pro Ala Glu Thr Ser Val Arg Leu Arg Ala
            20                  25                  30

Tyr Leu Asn Thr Pro Gly Leu Pro Val Cys Gln Asp His Leu Glu Phe
        35                  40                  45

Trp Glu Ser Val Phe Thr Gly Leu Thr His Ile Asp Ala His Phe Leu
    50                  55                  60

Ser Gln Thr Lys Gln Ala Gly Asp Asn Phe Pro Tyr Leu Val Ala Tyr
65                  70                  75                  80

Gln Ala Thr Val Cys Ala Arg Ala Lys Ala Pro Pro Pro Ser Trp Asp
                85                  90                  95

Gln Met Trp Lys Cys Leu Ile Arg Leu Lys Pro Thr Leu His Gly Pro
            100                 105                 110

Thr Pro Leu Leu Tyr Arg Leu Gly Ala Val Gln Asn Glu Val Thr Leu
        115                 120                 125

Thr His Pro Ile Thr Lys Phe Ile Met Ala Cys Met Ser Ala Asp Leu
    130                 135                 140

Glu Val Val Thr
145
```

<210> SEQ ID NO 18
<211> LENGTH: 156
<212> TYPE: PRT
<213> ORGANISM: Artificial
<220> FEATURE:
<223> OTHER INFORMATION: NS3 based platform domain 3

<400> SEQUENCE: 18

```
Ser Val Thr Val Pro His Pro Asn Ile Glu Glu Val Ala Leu Ser Asn
1               5                   10                  15

Thr Gly Glu Ile Pro Phe Tyr Gly Lys Ala Ile Pro Leu Glu Ala Ile
            20                  25                  30

Lys Gly Gly Arg His Leu Ile Phe Cys His Ser Lys Gln Leu Cys Asp
        35                  40                  45

Glu Leu Ala Ala Lys Leu Ser Ala Leu Gly Val Asn Ala Val Ala Tyr
    50                  55                  60

Tyr Arg Gly Leu Asp Val Ser Ile Ile Pro Thr Ser Gly Asp Val Val
65                  70                  75                  80

Val Val Ala Thr Asp Ala Leu Met Thr Gly Tyr Thr Gly Asp Phe Asp
                85                  90                  95

Ser Val Ile Asp Cys Asn Thr Cys Val Thr Gln Thr Val Asp Phe Ser
            100                 105                 110

Leu Asp Pro Thr Phe Thr Ile Glu Thr Thr Thr Val Pro Gln Asp Ala
        115                 120                 125

Val Ser Arg Ser Gln Met Gln Gly Arg Thr Gly Arg Gly Arg Gly Gly
    130                 135                 140

Ile Tyr Arg Phe Val Thr Pro Gly Glu Arg Pro Ser
145                 150                 155
```

```
<210> SEQ ID NO 19
<211> LENGTH: 180
<212> TYPE: PRT
<213> ORGANISM: Artificial
<220> FEATURE:
<223> OTHER INFORMATION: NS3 based platform domain 4

<400> SEQUENCE: 19

Thr Gly Ser Val Val Ile Val Gly Arg Ile Ile Leu Ser Gly Ile Thr
1               5                   10                  15

Ala Tyr Ser Gln Gln Thr Arg Gly Leu Leu Gly Cys Ile Ile Thr Ser
            20                  25                  30

Leu Thr Gly Arg Asp Lys Asn Gln Val Glu Gly Glu Val Gln Val Val
        35                  40                  45

Ser Thr Ala Thr Gln Ser Phe Leu Ala Thr Cys Ile Asn Gly Val Cys
    50                  55                  60

Trp Thr Val Tyr His Gly Ala Gly Ser Lys Thr Leu Ala Gly Pro Lys
65                  70                  75                  80

Gly Pro Ile Thr Gln Met Tyr Thr Asn Val Asp Gln Asp Leu Val Gly
                85                  90                  95

Trp Pro Ala Pro Pro Gly Ala Arg Ser Met Thr Pro Cys Thr Cys Gly
            100                 105                 110

Ser Ser Asp Leu Tyr Leu Val Thr Arg His Ala Asp Val Ile Pro Val
        115                 120                 125

Arg Gln Leu Gly Asp Ser Arg Gly Ser Leu Leu Ser Pro Arg Pro Ile
    130                 135                 140

Ser Tyr Leu Lys Gly Ser Ser Gly Gly Pro Leu Leu Cys Pro Ser Gly
145                 150                 155                 160

His Val Val Gly Ile Phe Arg Ala Ala Val Cys Thr Arg Gly Val Ala
                165                 170                 175

Lys Ala Val Asp
            180

<210> SEQ ID NO 20
<211> LENGTH: 14
<212> TYPE: PRT
<213> ORGANISM: Artificial
<220> FEATURE:
<223> OTHER INFORMATION: NS4A derived sequence in NS3 based platform
      domain 4

<400> SEQUENCE: 20

Thr Gly Ser Val Val Ile Val Gly Arg Ile Ile Leu Ser Gly
1               5                   10

<210> SEQ ID NO 21
<211> LENGTH: 9
<212> TYPE: PRT
<213> ORGANISM: Artificial
<220> FEATURE:
<223> OTHER INFORMATION: Modified epitope in NS3 based platform domain 3

<400> SEQUENCE: 21

Leu Ile Phe Cys His Ser Lys Gln Leu
1               5

<210> SEQ ID NO 22
<211> LENGTH: 20
<212> TYPE: PRT
<213> ORGANISM: Artificial
<220> FEATURE:
<223> OTHER INFORMATION: Modified epitope in NS3 based platform domain 4
```

```
<400> SEQUENCE: 22

Leu Tyr Leu Val Thr Arg His Ala Asp Val Ile Pro Val Arg Gln Leu
1               5                   10                  15

Gly Asp Ser Arg
            20

<210> SEQ ID NO 23
<211> LENGTH: 226
<212> TYPE: PRT
<213> ORGANISM: Artificial
<220> FEATURE:
<223> OTHER INFORMATION: NS3 synthetic polypeptide 1 based on platform
      domain 1

<400> SEQUENCE: 23

Ala Thr Gln Ser Phe Leu Ala Thr Cys Ile Asn Gly Val Cys Trp Thr
1               5                   10                  15

Val Tyr His Gly Ala Gly Ser Val Pro Val Glu Ser Met Glu Thr Thr
            20                  25                  30

Met Arg Ser Pro Val Phe Thr Asp Asn Ser Thr Pro Pro Ala Val Pro
        35                  40                  45

Gln Ser Phe Gln Val Ala His Leu His Ala Pro Thr Gly Ser Gly Lys
    50                  55                  60

Ser Thr Lys Val Pro Ala Ala Tyr Ala Ala Gln Gly Tyr Lys Val Leu
65                  70                  75                  80

Val Leu Asn Pro Ser Val Ala Ala Thr Leu Gly Phe Gly Ala Tyr Met
                85                  90                  95

Ser Lys Ala His Gly Val Asp Pro Asn Ile Arg Thr Gly Val Arg Thr
            100                 105                 110

Ile Thr Thr Gly Ala Pro Ile Thr Tyr Ser Thr Tyr Gly Lys Phe Leu
        115                 120                 125

Ala Asp Gly Gly Cys Ser Gly Gly Ala Tyr Asp Ile Ile Ile Cys Asp
    130                 135                 140

Glu Cys His Ser Thr Asp Ser Thr Ser Ile Leu Gly Ile Gly Thr Val
145                 150                 155                 160

Leu Asp Gln Ala Glu Thr Ala Gly Ala Arg Leu Val Val Leu Ala Thr
                165                 170                 175

Ala Thr Gly Glu Ile Pro Phe Tyr Gly Lys Ala Ile Pro Leu Asp Glu
            180                 185                 190

Leu Ala Ala Lys Leu Ser Ala Leu Gly Val Asn Ala Val Ala Thr Asp
        195                 200                 205

Ala Leu Met Thr Gly Tyr Thr Gly Asp Phe Asp Ser Val Ile Asp Cys
    210                 215                 220

Asn Thr
225

<210> SEQ ID NO 24
<211> LENGTH: 190
<212> TYPE: PRT
<213> ORGANISM: Artificial
<220> FEATURE:
<223> OTHER INFORMATION: NS3 synthetic polypeptide 2 based on platform
      domain 1
```

<400> SEQUENCE: 24

| Ala | Thr | Gln | Ser | Phe | Leu | Ala | Thr | Cys | Ile | Asn | Gly | Val | Cys | Trp | Thr |
| --- | --- | --- | --- | --- | --- | --- | --- | --- | --- | --- | --- | --- | --- | --- | --- |
| 1 | | | | 5 | | | | | 10 | | | | | 15 | |

Val Tyr His Gly Ala Gly Ser Val Pro Val Glu Ser Met Glu Thr Thr
            20                  25                  30

Met Arg Ser Pro Val Phe Thr Asp Asn Ser Thr Pro Pro Ala Val Pro
        35                  40                  45

Gln Ser Phe Gln Val Ala His Leu His Ala Pro Thr Gly Ser Gly Lys
    50                  55                  60

Ser Thr Lys Val Pro Ala Ala Tyr Ala Ala Gln Gly Tyr Lys Val Leu
65                  70                  75                  80

Val Leu Asn Pro Ser Val Ala Ala Thr Leu Gly Phe Gly Ala Tyr Met
                85                  90                  95

Ser Lys Ala His Gly Val Asp Pro Asn Ile Arg Thr Gly Val Arg Thr
            100                 105                 110

Ile Thr Thr Gly Ala Pro Ile Thr Tyr Ser Thr Tyr Gly Lys Phe Leu
        115                 120                 125

Ala Asp Gly Gly Cys Ser Gly Gly Ala Tyr Asp Ile Ile Cys Asp
    130                 135                 140

Glu Cys His Ser Thr Asp Ser Thr Ser Ile Leu Gly Ile Gly Thr Val
145                 150                 155                 160

Leu Asp Gln Ala Glu Thr Ala Gly Ala Arg Leu Val Val Leu Ala Thr
                165                 170                 175

Ala Thr Gly Glu Ile Pro Phe Tyr Gly Lys Ala Ile Pro Leu
            180                 185                 190

<210> SEQ ID NO 25
<211> LENGTH: 678
<212> TYPE: DNA
<213> ORGANISM: Artificial
<220> FEATURE:
<223> OTHER INFORMATION: NS3 synthetic polypeptide 1 gene,
      codon-optimized for Bifidobacterium
<220> FEATURE:
<221> NAME/KEY: CDS
<222> LOCATION: (1)..(678)

<400> SEQUENCE: 25

```
gcc acc cag tcc ttc ctg gcc acc tgc atc aac ggc gtc tgc tgg acc      48
Ala Thr Gln Ser Phe Leu Ala Thr Cys Ile Asn Gly Val Cys Trp Thr
1               5                   10                  15 gtc tac cac ggc gcc ggc tcc gtg ccg gtc gag tcc atg gag acg acc      96
Val Tyr His Gly Ala Gly Ser Val Pro Val Glu Ser Met Glu Thr Thr
            20                  25                  30 atg cgc agc ccg gtc ttc acg gac aac tcc acc ccg ccg gcc gtg ccg     144
Met Arg Ser Pro Val Phe Thr Asp Asn Ser Thr Pro Pro Ala Val Pro
        35                  40                  45 cag agc ttc cag gtc gcg cac ctg cac gcg ccg acc ggc tcc ggc aag     192
Gln Ser Phe Gln Val Ala His Leu His Ala Pro Thr Gly Ser Gly Lys
    50                  55                  60 tcc acc aag gtg ccg gcc gcc tac gcc gcg cag ggc tac aag gtc ctg     240
Ser Thr Lys Val Pro Ala Ala Tyr Ala Ala Gln Gly Tyr Lys Val Leu
65                  70                  75                  80 gtg ctg aac ccg tcc gtc gcc gcc acg ctc ggc ttc ggc gcc tac atg     288
Val Leu Asn Pro Ser Val Ala Ala Thr Leu Gly Phe Gly Ala Tyr Met
                85                  90                  95 tcc aag gcg cac ggc gtc gat ccg aac atc cgc acc ggc gtc cgc acc     336
Ser Lys Ala His Gly Val Asp Pro Asn Ile Arg Thr Gly Val Arg Thr
            100                 105                 110
```

-continued

```
atc acg acc ggc gcg ccg atc acc tac tcc acc tac ggc aag ttc ctg      384
Ile Thr Thr Gly Ala Pro Ile Thr Tyr Ser Thr Tyr Gly Lys Phe Leu
        115                 120                 125 gcc gat ggc ggc tgc tcc ggc ggc gcc tac gac atc atc atc tgc gac      432
Ala Asp Gly Gly Cys Ser Gly Gly Ala Tyr Asp Ile Ile Ile Cys Asp
130                 135                 140 gag tgc cac tcc acc gac tcc acc tcc atc ctg ggc atc ggc acc gtc      480
Glu Cys His Ser Thr Asp Ser Thr Ser Ile Leu Gly Ile Gly Thr Val
145                 150                 155                 160 ctg gac cag gcc gag acc gcc ggc gcc cgc ctg gtc gtg ctg gcc acc      528
Leu Asp Gln Ala Glu Thr Ala Gly Ala Arg Leu Val Val Leu Ala Thr
                165                 170                 175 gcc acc ggc gag atc ccg ttc tac ggc aag gcc atc ccg ctg gac gag      576
Ala Thr Gly Glu Ile Pro Phe Tyr Gly Lys Ala Ile Pro Leu Asp Glu
            180                 185                 190 ctg gcc gcc aag ctg agc gcg ctc ggc gtc aac gcc gtc gcc acc gac      624
Leu Ala Ala Lys Leu Ser Ala Leu Gly Val Asn Ala Val Ala Thr Asp
        195                 200                 205 gcg ctg atg acc ggc tac acc ggc gac ttc gac tcc gtg atc gac tgc      672
Ala Leu Met Thr Gly Tyr Thr Gly Asp Phe Asp Ser Val Ile Asp Cys
210                 215                 220 aac acc                                                               678
Asn Thr
225
```

<210> SEQ ID NO 26
<211> LENGTH: 226
<212> TYPE: PRT
<213> ORGANISM: Artificial
<220> FEATURE:
<223> OTHER INFORMATION: Synthetic Construct

<400> SEQUENCE: 26

```
Ala Thr Gln Ser Phe Leu Ala Thr Cys Ile Asn Gly Val Cys Trp Thr
1               5                   10                  15

Val Tyr His Gly Ala Gly Ser Val Pro Val Glu Ser Met Glu Thr Thr
            20                  25                  30

Met Arg Ser Pro Val Phe Thr Asp Asn Ser Thr Pro Pro Ala Val Pro
        35                  40                  45

Gln Ser Phe Gln Val Ala His Leu His Ala Pro Thr Gly Ser Gly Lys
    50                  55                  60

Ser Thr Lys Val Pro Ala Ala Tyr Ala Ala Gln Gly Tyr Lys Val Leu
65                  70                  75                  80

Val Leu Asn Pro Ser Val Ala Ala Thr Leu Gly Phe Gly Ala Tyr Met
                85                  90                  95

Ser Lys Ala His Gly Val Asp Pro Asn Ile Arg Thr Gly Val Arg Thr
            100                 105                 110

Ile Thr Thr Gly Ala Pro Ile Thr Tyr Ser Thr Tyr Gly Lys Phe Leu
        115                 120                 125

Ala Asp Gly Gly Cys Ser Gly Gly Ala Tyr Asp Ile Ile Ile Cys Asp
    130                 135                 140

Glu Cys His Ser Thr Asp Ser Thr Ser Ile Leu Gly Ile Gly Thr Val
145                 150                 155                 160

Leu Asp Gln Ala Glu Thr Ala Gly Ala Arg Leu Val Val Leu Ala Thr
                165                 170                 175

Ala Thr Gly Glu Ile Pro Phe Tyr Gly Lys Ala Ile Pro Leu Asp Glu
            180                 185                 190
```

```
Leu Ala Ala Lys Leu Ser Ala Leu Gly Val Asn Ala Val Ala Thr Asp
            195                 200                 205

Ala Leu Met Thr Gly Tyr Thr Gly Asp Phe Asp Ser Val Ile Asp Cys
    210                 215                 220

Asn Thr
225

<210> SEQ ID NO 27
<211> LENGTH: 570
<212> TYPE: DNA
<213> ORGANISM: Artificial
<220> FEATURE:
<223> OTHER INFORMATION: NS3 synthetic polypeptide 2 gene,
      codon-optimized for Bifidobacterium
<220> FEATURE:
<221> NAME/KEY: CDS
<222> LOCATION: (1)..(570)

<400> SEQUENCE: 27 gcc acc cag tcc ttc ctg gcc acc tgc atc aac ggc gtc tgc tgg acc      48
Ala Thr Gln Ser Phe Leu Ala Thr Cys Ile Asn Gly Val Cys Trp Thr
1               5                   10                  15 gtc tac cac ggc gcc ggc tcc gtg ccg gtc gag tcc atg gag acg acc      96
Val Tyr His Gly Ala Gly Ser Val Pro Val Glu Ser Met Glu Thr Thr
            20                  25                  30 atg cgc agc ccg gtc ttc acg gac aac tcc acc ccg gcc gtg ccg          144
Met Arg Ser Pro Val Phe Thr Asp Asn Ser Thr Pro Pro Ala Val Pro
        35                  40                  45 cag agc ttc cag gtc gcg cac ctg cac gcg ccg acc ggc tcc ggc aag      192
Gln Ser Phe Gln Val Ala His Leu His Ala Pro Thr Gly Ser Gly Lys
    50                  55                  60 tcc acc aag gtg ccg gcc gcc tac gcc gcg cag ggc tac aag gtc ctg      240
Ser Thr Lys Val Pro Ala Ala Tyr Ala Ala Gln Gly Tyr Lys Val Leu
65                  70                  75                  80 gtg ctg aac ccg tcc gtc gcc gcc acg ctc ggc ttc ggc gcc tac atg      288
Val Leu Asn Pro Ser Val Ala Ala Thr Leu Gly Phe Gly Ala Tyr Met
                85                  90                  95 tcc aag gcg cac ggc gtc gat ccg aac atc cgc acc ggc gtc cgc acc      336
Ser Lys Ala His Gly Val Asp Pro Asn Ile Arg Thr Gly Val Arg Thr
            100                 105                 110 atc acg acc ggc gcg ccg atc acc tac tcc acc tac ggc aag ttc ctg      384
Ile Thr Thr Gly Ala Pro Ile Thr Tyr Ser Thr Tyr Gly Lys Phe Leu
        115                 120                 125 gcc gat ggc ggc tgc tcc ggc ggc gcc tac gac atc atc atc tgc gac      432
Ala Asp Gly Gly Cys Ser Gly Gly Ala Tyr Asp Ile Ile Ile Cys Asp
    130                 135                 140 gag tgc cac tcc acc gac tcc acc tcc atc ctg ggc atc ggc acc gtc      480
Glu Cys His Ser Thr Asp Ser Thr Ser Ile Leu Gly Ile Gly Thr Val
145                 150                 155                 160 ctg gac cag gcc gag acc gcc ggc gcc cgc ctg gtc gtg ctg gcc acc      528
Leu Asp Gln Ala Glu Thr Ala Gly Ala Arg Leu Val Val Leu Ala Thr
                165                 170                 175 gcc acc ggc gag atc ccg ttc tac ggc aag gcc atc ccg ctg                570
Ala Thr Gly Glu Ile Pro Phe Tyr Gly Lys Ala Ile Pro Leu
            180                 185                 190

<210> SEQ ID NO 28
<211> LENGTH: 190
<212> TYPE: PRT
<213> ORGANISM: Artificial
<220> FEATURE:
<223> OTHER INFORMATION: Synthetic Construct
```

<400> SEQUENCE: 28

Ala Thr Gln Ser Phe Leu Ala Thr Cys Ile Asn Gly Val Cys Trp Thr
1               5                   10                  15

Val Tyr His Gly Ala Gly Ser Val Pro Val Glu Ser Met Glu Thr Thr
            20                  25                  30

Met Arg Ser Pro Val Phe Thr Asp Asn Ser Thr Pro Pro Ala Val Pro
        35                  40                  45

Gln Ser Phe Gln Val Ala His Leu His Ala Pro Thr Gly Ser Gly Lys
    50                  55                  60

Ser Thr Lys Val Pro Ala Ala Tyr Ala Ala Gln Gly Tyr Lys Val Leu
65                  70                  75                  80

Val Leu Asn Pro Ser Val Ala Ala Thr Leu Gly Phe Gly Ala Tyr Met
                85                  90                  95

Ser Lys Ala His Gly Val Asp Pro Asn Ile Arg Thr Gly Val Arg Thr
            100                 105                 110

Ile Thr Thr Gly Ala Pro Ile Thr Tyr Ser Thr Tyr Gly Lys Phe Leu
        115                 120                 125

Ala Asp Gly Gly Cys Ser Gly Gly Ala Tyr Asp Ile Ile Cys Asp
    130                 135                 140

Glu Cys His Ser Thr Asp Ser Thr Ser Ile Leu Gly Ile Gly Thr Val
145                 150                 155                 160

Leu Asp Gln Ala Glu Thr Ala Gly Ala Arg Leu Val Val Leu Ala Thr
                165                 170                 175

Ala Thr Gly Glu Ile Pro Phe Tyr Gly Lys Ala Ile Pro Leu
            180                 185                 190

<210> SEQ ID NO 29
<211> LENGTH: 38
<212> TYPE: DNA
<213> ORGANISM: Artificial
<220> FEATURE:
<223> OTHER INFORMATION: Forward primer for NS3 synthetic polypeptides
      1 and 2

<400> SEQUENCE: 29
ggaaaactgt ccatagatgg cgaggcgaac gccacggt                           38

<210> SEQ ID NO 30
<211> LENGTH: 39
<212> TYPE: DNA
<213> ORGANISM: Artificial
<220> FEATURE:
<223> OTHER INFORMATION: Reverse primer for SN3 synthetic polypeptide 1

<400> SEQUENCE: 30
tttcatctgt gcatagtcga cttcaggtgt tgcagtcga                          39

<210> SEQ ID NO 31
<211> LENGTH: 42
<212> TYPE: DNA
<213> ORGANISM: Artificial
<220> FEATURE:
<223> OTHER INFORMATION: Reverse primer for SN3 synthetic polypeptide 2

<400> SEQUENCE: 31
tttcatctgt gcatattcac agcgggatgg ccttgccgta ga                      42

<210> SEQ ID NO 32
<211> LENGTH: 219
<212> TYPE: PRT
<213> ORGANISM: Artificial
<220> FEATURE:
<223> OTHER INFORMATION: NS3 synthetic polypeptide 3 based on platform domain 2

<400> SEQUENCE: 32

```
Ala Thr Gln Ser Phe Leu Ala Thr Cys Ile Asn Gly Val Cys Trp Thr
1               5                   10                  15

Val Tyr His Gly Ala Gly Ser Gly Met Phe Asp Ser Ser Val Leu Cys
            20                  25                  30

Glu Cys Tyr Asp Ala Gly Cys Ala Trp Tyr Glu Leu Thr Pro Ala Glu
        35                  40                  45

Thr Ser Val Arg Leu Arg Ala Tyr Leu Asn Thr Pro Gly Leu Pro Val
    50                  55                  60

Cys Gln Asp His Leu Glu Phe Trp Glu Ser Val Phe Thr Gly Leu Thr
65                  70                  75                  80

His Ile Asp Ala His Phe Leu Ser Gln Thr Lys Gln Ala Gly Asp Asn
                85                  90                  95

Phe Pro Tyr Leu Val Ala Tyr Gln Ala Thr Val Cys Ala Arg Ala Lys
            100                 105                 110

Ala Pro Pro Pro Ser Trp Asp Gln Met Trp Lys Cys Leu Ile Arg Leu
        115                 120                 125

Lys Pro Thr Leu His Gly Pro Thr Pro Leu Leu Tyr Arg Leu Gly Ala
    130                 135                 140

Val Gln Asn Glu Val Thr Leu Thr His Pro Ile Thr Lys Phe Ile Met
145                 150                 155                 160

Ala Cys Met Ser Ala Asp Leu Glu Val Val Thr Gly Glu Ile Pro Phe
                165                 170                 175

Tyr Gly Lys Ala Ile Pro Leu Asp Glu Leu Ala Ala Lys Leu Ser Ala
            180                 185                 190

Leu Gly Val Asn Ala Val Ala Thr Asp Ala Leu Met Thr Gly Tyr Thr
        195                 200                 205

Gly Asp Phe Asp Ser Val Ile Asp Cys Asn Thr
    210                 215
```

<210> SEQ ID NO 33
<211> LENGTH: 657
<212> TYPE: DNA
<213> ORGANISM: Artificial
<220> FEATURE:
<223> OTHER INFORMATION: NS3 synthetic polypeptide 3 gene, codon-optimized for Bifidobacterium
<220> FEATURE:
<221> NAME/KEY: CDS
<222> LOCATION: (1)..(657)

<400> SEQUENCE: 33

```
gcc acc cag tcc ttc ctg gcc acc tgc atc aac ggc gtc tgc tgg acc      48
Ala Thr Gln Ser Phe Leu Ala Thr Cys Ile Asn Gly Val Cys Trp Thr
1               5                   10                  15 gtc tac cac ggc gcc ggc tcc ggc atg ttc gac tcc tcc gtc ctg tgc      96
Val Tyr His Gly Ala Gly Ser Gly Met Phe Asp Ser Ser Val Leu Cys
            20                  25                  30 gag tgc tac gac gcc ggc tgc gcc tgg tac gag ctg acc ccg gcc gag     144
Glu Cys Tyr Asp Ala Gly Cys Ala Trp Tyr Glu Leu Thr Pro Ala Glu
        35                  40                  45
```

```
acc tcc gtc cgc ctg cgc gcc tac ctg aac acc ccg ggc ctg ccg gtc      192
Thr Ser Val Arg Leu Arg Ala Tyr Leu Asn Thr Pro Gly Leu Pro Val
    50                  55                  60 tgc cag gac cac ctg gag ttc tgg gag tcc gtc ttc acc ggc ctg acc      240
Cys Gln Asp His Leu Glu Phe Trp Glu Ser Val Phe Thr Gly Leu Thr
65                  70                  75                  80 cac atc gac gcc cac ttc ctg tcc cag acc aag cag gcc ggc gac aac      288
His Ile Asp Ala His Phe Leu Ser Gln Thr Lys Gln Ala Gly Asp Asn
                85                  90                  95 ttc ccg tac ctg gtc gcc tac cag gcc acc gtc tgc gcc cgc gcc aag      336
Phe Pro Tyr Leu Val Ala Tyr Gln Ala Thr Val Cys Ala Arg Ala Lys
            100                 105                 110 gcc ccg ccg ccg tcc tgg gac cag atg tgg aag tgc ctg atc cgc ctg      384
Ala Pro Pro Pro Ser Trp Asp Gln Met Trp Lys Cys Leu Ile Arg Leu
        115                 120                 125 aag ccg acc ctg cac ggc ccg acc ccg ctg ctc tac cgc ctg ggc gcc      432
Lys Pro Thr Leu His Gly Pro Thr Pro Leu Leu Tyr Arg Leu Gly Ala
    130                 135                 140 gtc cag aac gag gtc acc ctg acc cac ccg atc acc aag ttc atc atg      480
Val Gln Asn Glu Val Thr Leu Thr His Pro Ile Thr Lys Phe Ile Met
145                 150                 155                 160 gcc tgc atg tcc gcc gac ctg gag gtc gtc acc ggc gag atc ccg ttc      528
Ala Cys Met Ser Ala Asp Leu Glu Val Val Thr Gly Glu Ile Pro Phe
                165                 170                 175 tac ggc aag gcc atc ccg ctg gac gag ctg gcc gcc aag ctg tcc gcc      576
Tyr Gly Lys Ala Ile Pro Leu Asp Glu Leu Ala Ala Lys Leu Ser Ala
            180                 185                 190 ctg ggc gtc aac gcc gtc gcc acc gac gcc ctg atg acc ggc tac acc      624
Leu Gly Val Asn Ala Val Ala Thr Asp Ala Leu Met Thr Gly Tyr Thr
        195                 200                 205 ggc gac ttc gac tcc gtc atc gac tgc aac acc                          657
Gly Asp Phe Asp Ser Val Ile Asp Cys Asn Thr
    210                 215

<210> SEQ ID NO 34
<211> LENGTH: 219
<212> TYPE: PRT
<213> ORGANISM: Artificial
<220> FEATURE:
<223> OTHER INFORMATION: Synthetic Construct

<400> SEQUENCE: 34

Ala Thr Gln Ser Phe Leu Ala Thr Cys Ile Asn Gly Val Cys Trp Thr
1               5                   10                  15

Val Tyr His Gly Ala Gly Ser Gly Met Phe Asp Ser Ser Val Leu Cys
                20                  25                  30

Glu Cys Tyr Asp Ala Gly Cys Ala Trp Tyr Glu Leu Thr Pro Ala Glu
            35                  40                  45

Thr Ser Val Arg Leu Arg Ala Tyr Leu Asn Thr Pro Gly Leu Pro Val
        50                  55                  60

Cys Gln Asp His Leu Glu Phe Trp Glu Ser Val Phe Thr Gly Leu Thr
65                  70                  75                  80

His Ile Asp Ala His Phe Leu Ser Gln Thr Lys Gln Ala Gly Asp Asn
                85                  90                  95

Phe Pro Tyr Leu Val Ala Tyr Gln Ala Thr Val Cys Ala Arg Ala Lys
            100                 105                 110

Ala Pro Pro Pro Ser Trp Asp Gln Met Trp Lys Cys Leu Ile Arg Leu
        115                 120                 125
```

```
Lys Pro Thr Leu His Gly Pro Thr Pro Leu Leu Tyr Arg Leu Gly Ala
    130                 135                 140

Val Gln Asn Glu Val Thr Leu Thr His Pro Ile Thr Lys Phe Ile Met
145                 150                 155                 160

Ala Cys Met Ser Ala Asp Leu Glu Val Val Thr Gly Glu Ile Pro Phe
                165                 170                 175

Tyr Gly Lys Ala Ile Pro Leu Asp Glu Leu Ala Ala Lys Leu Ser Ala
                180                 185                 190

Leu Gly Val Asn Ala Val Ala Thr Asp Ala Leu Met Thr Gly Tyr Thr
                195                 200                 205

Gly Asp Phe Asp Ser Val Ile Asp Cys Asn Thr
    210                 215
```

```
<210> SEQ ID NO 35
<211> LENGTH: 199
<212> TYPE: PRT
<213> ORGANISM: Artificial
<220> FEATURE:
<223> OTHER INFORMATION: NS3 synthetic polypeptide 4 based on platform
      domain 3

<400> SEQUENCE: 35

Ala Thr Gln Ser Phe Leu Ala Thr Cys Ile Asn Gly Val Cys Trp Thr
1               5                   10                  15

Val Tyr His Gly Ala Gly Ser Ser Val Thr Val Pro His Pro Asn Ile
                20                  25                  30

Glu Glu Val Ala Leu Ser Asn Thr Gly Glu Ile Pro Phe Tyr Gly Lys
            35                  40                  45

Ala Ile Pro Leu Glu Ala Ile Lys Gly Gly Arg His Leu Ile Phe Cys
    50                  55                  60

His Ser Lys Gln Leu Cys Asp Glu Leu Ala Ala Lys Leu Ser Ala Leu
65                  70                  75                  80

Gly Val Asn Ala Val Ala Tyr Tyr Arg Gly Leu Asp Val Ser Ile Ile
                85                  90                  95

Pro Thr Ser Gly Asp Val Val Val Ala Thr Asp Ala Leu Met Thr
                100                 105                 110

Gly Tyr Thr Gly Asp Phe Asp Ser Val Ile Asp Cys Asn Thr Cys Val
            115                 120                 125

Thr Gln Thr Val Asp Phe Ser Leu Asp Pro Thr Phe Thr Ile Glu Thr
    130                 135                 140

Thr Thr Val Pro Gln Asp Ala Val Ser Arg Ser Gln Met Gln Gly Arg
145                 150                 155                 160

Thr Gly Arg Gly Arg Gly Ile Tyr Arg Phe Val Thr Pro Gly Glu
                165                 170                 175

Arg Pro Ser Glu Leu Thr Pro Ala Glu Thr Ser Val Arg Leu Arg Ala
                180                 185                 190

Tyr Leu Asn Thr Pro Gly Leu
            195
```

```
<210> SEQ ID NO 36
<211> LENGTH: 597
<212> TYPE: DNA
<213> ORGANISM: Artificial
<220> FEATURE:
<223> OTHER INFORMATION: NS3 synthetic polypeptide 4 gene,
      codon-optimized for Bifidobacterium
<220> FEATURE:
<221> NAME/KEY: CDS
<222> LOCATION: (1)..(597)
```

<400> SEQUENCE: 36

```
gcc acc cag tcc ttc ctg gcc acc tgc atc aac ggc gtc tgc tgg acc      48
Ala Thr Gln Ser Phe Leu Ala Thr Cys Ile Asn Gly Val Cys Trp Thr
1               5                  10                  15 gtc tac cac ggc gcc ggc tcc tcc gtc acc gtc ccg cac ccg aac atc      96
Val Tyr His Gly Ala Gly Ser Ser Val Thr Val Pro His Pro Asn Ile
            20                  25                  30 gag gag gtc gcc ctg tcc aac acc ggc gag atc ccg ttc tac ggc aag     144
Glu Glu Val Ala Leu Ser Asn Thr Gly Glu Ile Pro Phe Tyr Gly Lys
        35                  40                  45 gcc atc ccg ctg gag gcc atc aag ggc ggc cgc cac ctg atc ttc tgc     192
Ala Ile Pro Leu Glu Ala Ile Lys Gly Gly Arg His Leu Ile Phe Cys
    50                  55                  60 cac tcc aag cag ctg tgc gac gag ctg gcc gcc aag ctg tcc gcc ctg     240
His Ser Lys Gln Leu Cys Asp Glu Leu Ala Ala Lys Leu Ser Ala Leu
65                  70                  75                  80 ggc gtc aac gcc gtc gcc tac tac cgc ggc ctg gac gtc tcc atc atc     288
Gly Val Asn Ala Val Ala Tyr Tyr Arg Gly Leu Asp Val Ser Ile Ile
                85                  90                  95 ccg acc tcc ggc gac gtc gtc gtc gcc acc gac gcc ctg atg acc         336
Pro Thr Ser Gly Asp Val Val Val Ala Thr Asp Ala Leu Met Thr
            100                 105                 110 ggc tac acc ggc gac ttc gac tcc gtc atc gac tgc aac acc tgc gtc     384
Gly Tyr Thr Gly Asp Phe Asp Ser Val Ile Asp Cys Asn Thr Cys Val
        115                 120                 125 acc cag acc gtc gac ttc tcc ctg gac ccg acc ttc acc atc gag acc     432
Thr Gln Thr Val Asp Phe Ser Leu Asp Pro Thr Phe Thr Ile Glu Thr
    130                 135                 140 acc acc gtc ccg cag gac gcc gtc tcc cgc tcc cag atg cag ggc cgc     480
Thr Thr Val Pro Gln Asp Ala Val Ser Arg Ser Gln Met Gln Gly Arg
145                 150                 155                 160 acc ggc cgc ggc cgc ggc ggc atc tac cgc ttc gtc acc ccg ggc gag     528
Thr Gly Arg Gly Arg Gly Gly Ile Tyr Arg Phe Val Thr Pro Gly Glu
                165                 170                 175 cgc ccg tcc gag ctg acc ccg gcc gag acc tcc gtc cgc ctg cgc gcc     576
Arg Pro Ser Glu Leu Thr Pro Ala Glu Thr Ser Val Arg Leu Arg Ala
            180                 185                 190 tac ctg aac acc ccg ggc ctg                                          597
Tyr Leu Asn Thr Pro Gly Leu
        195
```

<210> SEQ ID NO 37
<211> LENGTH: 199
<212> TYPE: PRT
<213> ORGANISM: Artificial
<220> FEATURE:
<223> OTHER INFORMATION: Synthetic Construct

<400> SEQUENCE: 37

```
Ala Thr Gln Ser Phe Leu Ala Thr Cys Ile Asn Gly Val Cys Trp Thr
1               5                  10                  15

Val Tyr His Gly Ala Gly Ser Ser Val Thr Val Pro His Pro Asn Ile
            20                  25                  30

Glu Glu Val Ala Leu Ser Asn Thr Gly Glu Ile Pro Phe Tyr Gly Lys
        35                  40                  45

Ala Ile Pro Leu Glu Ala Ile Lys Gly Gly Arg His Leu Ile Phe Cys
    50                  55                  60

His Ser Lys Gln Leu Cys Asp Glu Leu Ala Ala Lys Leu Ser Ala Leu
65                  70                  75                  80
```

```
Gly Val Asn Ala Val Ala Tyr Tyr Arg Gly Leu Asp Val Ser Ile Ile
                85                  90                  95

Pro Thr Ser Gly Asp Val Val Val Ala Thr Asp Ala Leu Met Thr
            100                 105                 110

Gly Tyr Thr Gly Asp Phe Asp Ser Val Ile Asp Cys Asn Thr Cys Val
            115                 120                 125

Thr Gln Thr Val Asp Phe Ser Leu Asp Pro Thr Phe Thr Ile Glu Thr
        130                 135                 140

Thr Thr Val Pro Gln Asp Ala Val Ser Arg Ser Gln Met Gln Gly Arg
145                 150                 155                 160

Thr Gly Arg Gly Arg Gly Gly Ile Tyr Arg Phe Val Thr Pro Gly Glu
            165                 170                 175

Arg Pro Ser Glu Leu Thr Pro Ala Glu Thr Ser Val Arg Leu Arg Ala
            180                 185                 190

Tyr Leu Asn Thr Pro Gly Leu
            195
```

<210> SEQ ID NO 38
<211> LENGTH: 384
<212> TYPE: PRT
<213> ORGANISM: Artificial
<220> FEATURE:
<223> OTHER INFORMATION: NS3 synthetic polypeptide 5 based on platform domain 4

<400> SEQUENCE: 38

```
Thr Gly Ser Val Val Ile Val Gly Arg Ile Ile Leu Ser Gly Ile Thr
1               5                   10                  15

Ala Tyr Ser Gln Gln Thr Arg Gly Leu Leu Gly Cys Ile Ile Thr Ser
                20                  25                  30

Leu Thr Gly Arg Asp Lys Asn Gln Val Glu Gly Glu Val Gln Val Val
            35                  40                  45

Ser Thr Ala Thr Gln Ser Phe Leu Ala Thr Cys Ile Asn Gly Val Cys
        50                  55                  60

Trp Thr Val Tyr His Gly Ala Gly Ser Lys Thr Leu Ala Gly Pro Lys
65                  70                  75                  80

Gly Pro Ile Thr Gln Met Tyr Thr Asn Val Asp Gln Asp Leu Val Gly
                85                  90                  95

Trp Pro Ala Pro Pro Gly Ala Arg Ser Met Thr Pro Cys Thr Cys Gly
            100                 105                 110

Ser Ser Asp Leu Tyr Leu Val Thr Arg His Ala Asp Val Ile Pro Val
        115                 120                 125

Arg Gln Leu Gly Asp Ser Arg Gly Ser Leu Leu Ser Pro Arg Pro Ile
130                 135                 140

Ser Tyr Leu Lys Gly Ser Ser Gly Gly Pro Leu Leu Cys Pro Ser Gly
145                 150                 155                 160

His Val Val Gly Ile Phe Arg Ala Ala Val Cys Thr Arg Gly Val Ala
                165                 170                 175

Lys Ala Val Asp Phe Val Pro Val Glu Ser Met Glu Thr Thr Met Arg
            180                 185                 190

Ser Pro Val Phe Thr Asp Asn Ser Thr Pro Pro Ala Val Pro Gln Ser
        195                 200                 205

Phe Gln Val Ala His Leu His Ala Pro Thr Gly Ser Gly Lys Ser Thr
    210                 215                 220

Lys Val Pro Ala Ala Tyr Ala Ala Gln Gly Tyr Lys Val Leu Val Leu
225                 230                 235                 240
```

-continued

```
Asn Pro Ser Val Ala Ala Thr Leu Gly Phe Gly Ala Tyr Met Ser Lys
            245                 250                 255
Ala His Gly Val Asp Pro Asn Ile Arg Thr Gly Val Arg Thr Ile Thr
        260                 265                 270
Thr Gly Ala Pro Ile Thr Tyr Ser Thr Tyr Gly Lys Phe Leu Ala Asp
    275                 280                 285
Gly Gly Cys Ser Gly Gly Ala Tyr Asp Ile Ile Ile Cys Asp Glu Cys
290                 295                 300
His Ser Thr Asp Ser Thr Ser Ile Leu Gly Ile Gly Thr Val Leu Asp
305                 310                 315                 320
Gln Ala Glu Thr Ala Gly Ala Arg Leu Val Val Leu Ala Thr Ala Thr
            325                 330                 335
Gly Glu Ile Pro Phe Tyr Gly Lys Ala Ile Pro Leu Asp Glu Leu Ala
        340                 345                 350
Ala Lys Leu Ser Ala Leu Gly Val Asn Ala Val Ala Thr Asp Ala Leu
    355                 360                 365
Met Thr Gly Tyr Thr Gly Asp Phe Asp Ser Val Ile Asp Cys Asn Thr
370                 375                 380
```

<210> SEQ ID NO 39
<211> LENGTH: 1152
<212> TYPE: DNA
<213> ORGANISM: Artificial
<220> FEATURE:
<223> OTHER INFORMATION: NS3 synthetic polypeptide 5 gene,
      codon-optimized for Bifidobacterium
<220> FEATURE:
<221> NAME/KEY: CDS
<222> LOCATION: (1)..(1152)

<400> SEQUENCE: 39

```
acc ggc tcc gtc gtc atc gtc ggc cgc atc atc ctg tcc ggc atc acc        48
Thr Gly Ser Val Val Ile Val Gly Arg Ile Ile Leu Ser Gly Ile Thr
1               5                   10                  15 gcc tac tcc cag cag acc cgc ggc ctg ctg ggc tgc atc atc acc tcc        96
Ala Tyr Ser Gln Gln Thr Arg Gly Leu Leu Gly Cys Ile Ile Thr Ser
            20                  25                  30 ctg acc ggc cgc gac aag aac cag gtc gag ggc gag gtc cag gtc gtc       144
Leu Thr Gly Arg Asp Lys Asn Gln Val Glu Gly Glu Val Gln Val Val
        35                  40                  45 tcc acc gcc acc cag tcc ttc ctg gcc acc tgc atc aac ggc gtc tgc       192
Ser Thr Ala Thr Gln Ser Phe Leu Ala Thr Cys Ile Asn Gly Val Cys
    50                  55                  60 tgg acc gtc tac cac ggc gcc ggc tcc aag acc ctg gcc ggc ccg aag       240
Trp Thr Val Tyr His Gly Ala Gly Ser Lys Thr Leu Ala Gly Pro Lys
65                  70                  75                  80 ggc ccg atc acc cag atg tac acc aac gtc gac cag gac ctg gtc ggc       288
Gly Pro Ile Thr Gln Met Tyr Thr Asn Val Asp Gln Asp Leu Val Gly
                85                  90                  95 tgg ccg gcc ccg ccg ggc gcc cgc tcc atg acc ccg tgc acc tgc ggc       336
Trp Pro Ala Pro Pro Gly Ala Arg Ser Met Thr Pro Cys Thr Cys Gly
            100                 105                 110 tcc tcc gac ctg tac ctg gtc acc cgc cac gcc gac gtc atc ccg gtc       384
Ser Ser Asp Leu Tyr Leu Val Thr Arg His Ala Asp Val Ile Pro Val
        115                 120                 125 cgc cag ctg ggc gac tcc cgc ggc tcc ctg ctg tcc ccg cgc ccg atc       432
Arg Gln Leu Gly Asp Ser Arg Gly Ser Leu Leu Ser Pro Arg Pro Ile
    130                 135                 140
```

```
tcc tac ctg aag ggc tcc tcc ggc ggc ccg ctg ctg tgc ccg tcc ggc      480
Ser Tyr Leu Lys Gly Ser Ser Gly Gly Pro Leu Leu Cys Pro Ser Gly
145                 150                 155                 160 cac gtc gtc ggc atc ttc cgc gcc gcc gtc tgc acc cgc ggc gtc gcc      528
His Val Val Gly Ile Phe Arg Ala Ala Val Cys Thr Arg Gly Val Ala
                165                 170                 175 aag gcc gtc gac ttc gtg ccg gtc gag tcc atg gag acg acc atg cgc      576
Lys Ala Val Asp Phe Val Pro Val Glu Ser Met Glu Thr Thr Met Arg
            180                 185                 190 agc ccg gtc ttc acg gac aac tcc acc ccg ccg gcc gtg ccg cag agc      624
Ser Pro Val Phe Thr Asp Asn Ser Thr Pro Pro Ala Val Pro Gln Ser
        195                 200                 205 ttc cag gtc gcg cac ctg cac gcg ccg acc ggc tcc ggc aag tcc acc      672
Phe Gln Val Ala His Leu His Ala Pro Thr Gly Ser Gly Lys Ser Thr
    210                 215                 220 aag gtg ccg gcc gcc tac gcc gcg cag ggc tac aag gtc ctg gtg ctg      720
Lys Val Pro Ala Ala Tyr Ala Ala Gln Gly Tyr Lys Val Leu Val Leu
225                 230                 235                 240 aac ccg tcc gtc gcc gcc acg ctc ggc ttc ggc gcc tac atg tcc aag      768
Asn Pro Ser Val Ala Ala Thr Leu Gly Phe Gly Ala Tyr Met Ser Lys
                245                 250                 255 gcg cac ggc gtc gat ccg aac atc cgc acc ggc gtc cgc acc atc acg      816
Ala His Gly Val Asp Pro Asn Ile Arg Thr Gly Val Arg Thr Ile Thr
            260                 265                 270 acc ggc gcg ccg atc acc tac tcc acc tac ggc aag ttc ctg gcc gat      864
Thr Gly Ala Pro Ile Thr Tyr Ser Thr Tyr Gly Lys Phe Leu Ala Asp
        275                 280                 285 ggc ggc tgc tcc ggc ggc gcc tac gac atc atc atc tgc gac gag tgc      912
Gly Gly Cys Ser Gly Gly Ala Tyr Asp Ile Ile Ile Cys Asp Glu Cys
    290                 295                 300 cac tcc acc gac tcc acc tcc atc ctg ggc atc ggc acc gtc ctg gac      960
His Ser Thr Asp Ser Thr Ser Ile Leu Gly Ile Gly Thr Val Leu Asp
305                 310                 315                 320 cag gcc gag acc gcc ggc gcc cgc ctg gtc gtg ctg gcc acc gcc acc     1008
Gln Ala Glu Thr Ala Gly Ala Arg Leu Val Val Leu Ala Thr Ala Thr
                325                 330                 335 ggc gag atc ccg ttc tac ggc aag gcc atc ccg ctg gac gag ctg gcc     1056
Gly Glu Ile Pro Phe Tyr Gly Lys Ala Ile Pro Leu Asp Glu Leu Ala
            340                 345                 350 gcc aag ctg agc gcg ctc ggc gtc aac gcc gtc gcc acc gac gcg ctg     1104
Ala Lys Leu Ser Ala Leu Gly Val Asn Ala Val Ala Thr Asp Ala Leu
        355                 360                 365 atg acc ggc tac acc ggc gac ttc gac tcc gtg atc gac tgc aac acc     1152
Met Thr Gly Tyr Thr Gly Asp Phe Asp Ser Val Ile Asp Cys Asn Thr
    370                 375                 380

<210> SEQ ID NO 40
<211> LENGTH: 384
<212> TYPE: PRT
<213> ORGANISM: Artificial
<220> FEATURE:
<223> OTHER INFORMATION: Synthetic Construct

<400> SEQUENCE: 40

Thr Gly Ser Val Val Ile Val Gly Arg Ile Ile Leu Ser Gly Ile Thr
1               5                   10                  15

Ala Tyr Ser Gln Gln Thr Arg Gly Leu Leu Gly Cys Ile Ile Thr Ser
            20                  25                  30
```

Leu Thr Gly Arg Asp Lys Asn Gln Val Glu Gly Val Gln Val Val
            35                  40                  45

Ser Thr Ala Thr Gln Ser Phe Leu Ala Thr Cys Ile Asn Gly Val Cys
 50                  55                  60

Trp Thr Val Tyr His Gly Ala Gly Ser Lys Thr Leu Ala Gly Pro Lys
 65                  70                  75                  80

Gly Pro Ile Thr Gln Met Tyr Thr Asn Val Asp Gln Asp Leu Val Gly
                 85                  90                  95

Trp Pro Ala Pro Pro Gly Ala Arg Ser Met Thr Pro Cys Thr Cys Gly
            100                 105                 110

Ser Ser Asp Leu Tyr Leu Val Thr Arg His Ala Asp Val Ile Pro Val
            115                 120                 125

Arg Gln Leu Gly Asp Ser Arg Gly Ser Leu Leu Ser Pro Arg Pro Ile
            130                 135                 140

Ser Tyr Leu Lys Gly Ser Ser Gly Gly Pro Leu Leu Cys Pro Ser Gly
145                 150                 155                 160

His Val Val Gly Ile Phe Arg Ala Ala Val Cys Thr Arg Gly Val Ala
                165                 170                 175

Lys Ala Val Asp Phe Val Pro Val Glu Ser Met Glu Thr Thr Met Arg
            180                 185                 190

Ser Pro Val Phe Thr Asp Asn Ser Thr Pro Pro Ala Val Pro Gln Ser
            195                 200                 205

Phe Gln Val Ala His Leu His Ala Pro Thr Gly Ser Gly Lys Ser Thr
            210                 215                 220

Lys Val Pro Ala Ala Tyr Ala Ala Gln Gly Tyr Lys Val Leu Val Leu
225                 230                 235                 240

Asn Pro Ser Val Ala Ala Thr Leu Gly Phe Gly Ala Tyr Met Ser Lys
                245                 250                 255

Ala His Gly Val Asp Pro Asn Ile Arg Thr Gly Val Arg Thr Ile Thr
            260                 265                 270

Thr Gly Ala Pro Ile Thr Tyr Ser Thr Tyr Gly Lys Phe Leu Ala Asp
            275                 280                 285

Gly Gly Cys Ser Gly Gly Ala Tyr Asp Ile Ile Cys Asp Glu Cys
            290                 295                 300

His Ser Thr Asp Ser Thr Ser Ile Leu Gly Ile Gly Thr Val Leu Asp
305                 310                 315                 320

Gln Ala Glu Thr Ala Gly Ala Arg Leu Val Val Leu Ala Thr Ala Thr
                325                 330                 335

Gly Glu Ile Pro Phe Tyr Gly Lys Ala Ile Pro Leu Asp Glu Leu Ala
            340                 345                 350

Ala Lys Leu Ser Ala Leu Gly Val Asn Ala Val Ala Thr Asp Ala Leu
            355                 360                 365

Met Thr Gly Tyr Thr Gly Asp Phe Asp Ser Val Ile Asp Cys Asn Thr
            370                 375                 380

<210> SEQ ID NO 41
<211> LENGTH: 26
<212> TYPE: DNA
<213> ORGANISM: Artificial Sequence
<220> FEATURE:
<223> OTHER INFORMATION: NS3/4 forward primer

<400> SEQUENCE: 41
cggccctcag gcatgttcga ttcttc                                           26

```
<210> SEQ ID NO 42
<211> LENGTH: 27
<212> TYPE: DNA
<213> ORGANISM: Artificial Sequence
<220> FEATURE:
<223> OTHER INFORMATION: NS3/4 reverse primer

<400> SEQUENCE: 42
ccggacaaga tgatcctgcc cacaatg                                          27
```